United States Patent
D'Orchymont et al.

(10) Patent No.: US 7,482,342 B2
(45) Date of Patent: Jan. 27, 2009

(54) INDAZOLECARBOXAMIDE DERIVATIVES, PREPARATION AND USE THEREOF AS CDK1, CDK2 AND CDK4 INHIBITORS

(75) Inventors: Hugues D'Orchymont, Strasbourg (FR); Luc Van Hijfte, Belbeuf (FR); Andre Zimmermann, Achenheim (FR)

(73) Assignee: sanofi-aventis, Paris (FR)

( * ) Notice: Subject to any disclaimer, the term of this patent is extended or adjusted under 35 U.S.C. 154(b) by 588 days.

(21) Appl. No.: 11/096,375

(22) Filed: Apr. 1, 2005

(65) Prior Publication Data

US 2006/0004000 A1 Jan. 5, 2006

Related U.S. Application Data

(63) Continuation of application No. PCT/FR03/02862, filed on Sep. 30, 2003.

(30) Foreign Application Priority Data

Oct. 2, 2002 (FR) .................... 02 12188

(51) Int. Cl.
- A61K 31/5377 (2006.01)
- A61K 31/506 (2006.01)
- A61K 31/4709 (2006.01)
- C07D 413/02 (2006.01)

(52) U.S. Cl. .................... 514/232.5; 514/338; 514/406; 514/256; 514/314; 514/310; 544/140; 544/333; 546/275.7; 548/362.5

(58) Field of Classification Search .................... None
See application file for complete search history.

(56) References Cited

U.S. PATENT DOCUMENTS 3,457,269 A 7/1969 Kirchner 7,294,644 B2 * 11/2007 Mayweg et al. ............. 514/399

FOREIGN PATENT DOCUMENTS

| EP | 0 410 509 A1 | 1/1991 |
| WO | WO 94/05642 | 3/1994 |
| WO | WO 01/85726 A1 | 11/2001 |
| WO | WO 2004/014864 | 2/2004 |
| WO | WO 2004/014922 | 2/2004 |

OTHER PUBLICATIONS

Hannig E et al, Zur Darstellung einiger Derivate der 5-Methylindazole-3-carbonsaure, Pharmazie, Veb Verlag Volk und Gesundheit. Berlin, DD, vol. 28, No. H 11/12, 1973, pp. 720-721.

* cited by examiner

Primary Examiner—Kamal A Saeed
(74) Attorney, Agent, or Firm—Ronald G. Ort

(57) ABSTRACT

Compound corresponding to general formula (I):

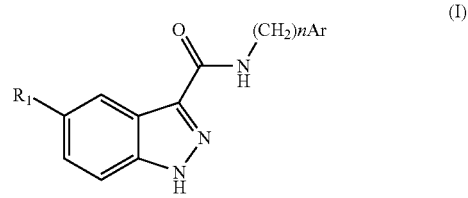

in which, $R_1$ represents a hydrogen or halogen atom, an $NH_2$, $NHR_2$, $NHCOR_2$, $NO_2$, $CN$, $CH_2NH_2$ and $CH_2NHR_2$; or alternatively $R_1$ represents an optionally substituted phenyl or an optionally substituted heteroaromatic group;
Ar represents an optionally substituted phenyl group or an optionally substituted heteroaromatic group;
n represents 0, 1, 2 or 3;
in the form of a base, of an addition salt with an acid, of a hydrate or of a solvate. Application in therapy.

13 Claims, No Drawings

INDAZOLECARBOXAMIDE DERIVATIVES, PREPARATION AND USE THEREOF AS CDK1, CDK2 AND CDK4 INHIBITORS

CROSS-REFERENCE TO RELATED APPLICATIONS

This application is a continuation of WO Application No. PCT/FR03/002862, filed Sep. 30, 2003, which, in turn, claims the benefit of priority of French Application No. 02/12188, filed Oct. 2, 2002.

BACKGROUND OF THE INVENTION

The subject of the invention is 1H-indazole-3-carboxamide derivatives, their preparation and their use in therapy.

Certain 1H-indazole-3-carboxamide derivatives have been described in the prior art.

N-(4-Methylbenzyl)-1H-indazole-3-carboxamide has been described in J. Gen. Chem. USSR, 32, 78 (1962) and has shown no pharmacological activity. Moreover, U.S. Pat. No. 3,457,269 describes 1H-indazole-3-carboxamides which are useful as hypotensive agents.

A need still exists for finding and developing products which are inhibitors of cycline dependent kinases (cdks) such as cdk1, cdk2 and cdk4.

SUMMARY OF THE INVENTION

The invention satisfies this aim by providing 1H-indazole-3-carboxamide derivatives which exhibit cdk1, cdk2 and cdk4 inhibiting effects.

The first subject of the invention is compounds corresponding to general formula (I):

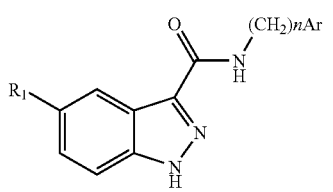

in which, $R_1$ represents a hydrogen or halogen atom, $NH_2$, $NHR_2$, $NHCOR_2$, $NO_2$, CN, $CH_2NH_2$ or $CH_2NHR_2$;

or alternatively $R_1$ represents a phenyl optionally substituted with one or two substituents chosen from a halogen atom, a hydroxyl, $C_{1-6}$ alkyl, $C_{1-6}$ alkoxy, $NH_2$, $NHR_2$ and $NR_2R_3$;

or alternatively $R_1$ represents a heteroaromatic group optionally substituted with one or two substituents chosen from a halogen atom, hydroxyl, a heteroaromatic group, $C_{1-6}$ alkyl, $NH_2$, $NHR_2$, $NHCOR_2$, $COOR_2$, $CONH_2$, $CONHR_2$ and $CH_2XR_2$ where X represents an atom chosen from O, NH and S;

Ar represents a phenyl group optionally substituted with one or two substituents chosen from a halogen atom, $C_{1-6}$ alkyl, $C_{1-6}$ thioalkyl, $C_{1-6}$ alkoxy, $CH_2OH$, phenoxy, morpholinyl, —$CH_2$-morpholinyl, $NH_2$, $NHR_2$, $NR_2R_3$, $NHSO_2R_2$, CN, $SO_2R_2$, $SO_2NH_2$, $SO_2NHR_2$, COOH, $COOR_2$, $CONH_2$, $CONHNH_2$, $CONHR_2$, $CH_2NHR_2$ and $CH_2NR_2R_3$;

or alternatively Ar represents a heteroaromatic group, optionally substituted with one or two substituents chosen from a halogen atom, $C_{1-6}$ alkyl, $C_{1-6}$ thioalkyl, $C_{1-6}$ alkoxy, $CH_2OH$, phenoxy, morpholinyl, —$CH_2$-morpholinyl, $NH_2$, $NHR_2$, $NR_2R_3$, $NHSO_2R_2$, CN, $SO_2R_2$, $SO_2NH_2$, $SO_2NHR_2$, COOH, $COOR_2$, $CONH_2$, $CONHNH_2$, $CONHR_2$, $CH_2NHR_2$ and $CH_2NR_2R_3$;

$R_2$ and $R_3$ represent, independently of each other, a $C_{1-6}$ alkyl optionally substituted with a group $CONH_2$, with a phenyl or with a heteroaromatic group; or $R_2$ and $R_3$ represent, independently of each other, a phenyl or a heteroaromatic group;

n represents 0, 1, 2 or 3.

The following compounds do not form part of the invention:

—N-phenyl-1H-indazole-3-carboxamide;
—N-(2-chlorophenyl)-1H-indazole-3-carboxamide;
—N-(3-chlorophenyl)-1H-indazole-3-carboxamide;
—N-(4-chlorophenyl)-1H-indazole-3-carboxamide;
—N-(2,4-dichlorophenyl)-1H-indazole-3-carboxamide;
—N-(3,4-dichlorophenyl)-1H-indazole-3-carboxamide;
—N-(2-methylphenyl)-1H-indazole-3-carboxamide;
—N-(2-methoxyphenyl)-1H-indazole-3-carboxamide;
—N-(4-methoxyphenyl)-1H-indazole-3-carboxamide;
—N-(4-thiomethylphenyl)-1H-indazole-3-carboxamide;
—N-(3-chloro-4-thiomethylphenyl)-5-amino-1H-indazole-3-carboxamide;
—N-benzyl-1H-indazole-3-carboxamide;
—N-(2-chlorobenzyl)-1H-indazole-3-carboxamide;
—N-(4-methylbenzyl)-1H-indazole-3-carboxamide;
—N-(pyridin-2-ylmethyl)-1H-indazole-3-carboxamide;
—N-(pyridin-3-ylmethyl)-1H-indazole-3-carboxamide;
—N-(pyridin-4-ylmethyl)-1H-indazole-3-carboxamide;
—N-(2-phenylethyl)-1H-indazole-3-carboxamide;
—N-(3,4-dimethoxyphenylethyl)-1H-indazole-3-carboxamide;
—N-[3-(pyridin-2-yl)propyl]-1H-indazole-3-carboxamide;
—N-[3-(2,6-dimethylphenyl)propyl]-5-nitro-1H-indazole-3-carboxamide.

DETAILED DESCRIPTION OF THE INVENTION

Among the compounds of general formula (I), a first family of preferred compounds consists of the compounds for which:

$R_1$ represents a hydrogen or halogen atom, $NH_2$, $NHR_2$, $NHCOR_2$, $NO_2$, CN, $CH_2NH_2$ or $CH_2NHR_2$;

or alternatively $R_1$ represents a phenyl optionally substituted with one or two substituents chosen from a halogen atom, hydroxyl, $C_{1-4}$ alkyl, $C_{1-6}$ alkoxy, $NH_2$, $NHR_2$ and $NR_2R_3$;

or alternatively $R_1$ represents a heteroaromatic group optionally substituted with one or two substituents chosen from a halogen atom, hydroxyl, a heteroaromatic group, $C_{1-6}$ alkyl, $NH_2$, $NHR_2$, $NHCOR_2$, $COOR_2$, $CONH_2$, $CONHR_2$ and $CH_2XR_2$ where X represents an atom chosen from O, N and S; and/or Ar represents a phenyl group optionally substituted with one or two substituents chosen from a halogen atom, $C_{1-6}$ alkyl, $C_{1-6}$ thioalkyl, $C_{1-6}$ alkoxy, $CH_2OH$, phenoxy, morpholinyl, —$CH_2$-morpholinyl, $NH_2$, $NHR_2$, $NR_2R_3$, $NHSO_2R_2$, CN, $SO_2R_2$, $SO_2NH_2$, $SO_2NHR_2$, COOH, $COOR_2$, $CONH_2$, $CONHNH_2$, $CONHR_2$, $CH_2NHR_2$ and $CH_2NR_2R_3$;

or alternatively Ar represents a heteroaromatic group, optionally substituted with one or two substituents chosen from a halogen atom, $C_{1-6}$ alkyl, $C_{1-6}$ thioalkyl, $C_{1-6}$ alkoxy, $CH_2OH$, phenoxy, morpholinyl, —$CH_2$-morpholinyl, $NH_2$, $NHR_2$, $NR_2R_3$, $NHSO_2R_2$, CN, $SO_2R_2$, $SO_2NH_2$, $SO_2NHR_2$, COOH, $COOR_2$, $CONH_2$, $CONHNH_2$, $CONHR_2$, $CH_2NHR_2$ and $CH_2NR_2R_3$; and/or $R_2$ and $R_3$ represent, independently of each other, a $C_{1-6}$ alkyl optionally substituted with a group $CONH_2$, with a phenyl or with a heteroaromatic group; or $R_2$ and $R_3$ represent, independently of each other, a phenyl or a heteroaromatic group; and/or n represents 0, 1, 2 or 3;

with the condition that when $R_1$ represents a hydrogen atom if n represents 0 and Ar is a phenyl, then the phenyl is necessarily substituted as defined above, the methyl, methoxy, thiomethyl and chlorine atom substituents being excluded;

if n represents 1, and then Ar is a phenyl, then the phenyl is necessarily substituted as defined above, the methyl and chlorine atom substituents being excluded;

if n represents 1, and then Ar is a pyridinyl, then the pyridinyl is necessarily substituted as defined above;

if n represents 2 and Ar is a phenyl, then the phenyl is necessarily substituted as defined above, the methoxy substituent being excluded;

if n represents 3 and Ar is a pyridinyl, then the pyridinyl is necessarily substituted as defined above;

when $R_1$ represents an $NH_2$ if n represents 0 and Ar is a phenyl, then the substituent(s) of the phenyl cannot be chosen from a thiomethyl or a chlorine atom;

when $R_1$ represents an $NO_2$ if n represents 3 and Ar is a phenyl, then the substituent(s) of the phenyl of Ar cannot be a methyl.

Among the compounds of general formula (I), a second family of preferred compounds consists of the compounds for which:

when $R_1$ represents a hydrogen atom, then Ar represents a phenyl group substituted with one or two substituents chosen from a bromine or iodine atom, $C_{2-6}$ alkyl, $C_{2-6}$ thioalkyl, $C_{2-6}$ alkoxy, $CH_2OH$, phenoxy, morpholinyl, —$CH_2$-morpholinyl, $NH_2$, $NHR_2$, $NR_2R_3$, $NHSO_2R_2$, CN, $SO_2R_2$, $SO_2NH_2$, $SO_2NHR_2$, COOH, $COOR_2$, $CONH_2$, $CONHNH_2$, $CONHR_2$, $CH_2NHR_2$ and $CH_2NR_2R_3$;

or alternatively Ar represents a heteroaromatic group chosen from pyrrolyl, imidazolyl, pyrazolyl, triazolyl, tetrazolyl, thiazolyl, isothiazolyl, 1,3,4-thiadiazol-yl, oxazolyl, isoxazolyl, oxadiazolyl, pyridazinyl, pirimidinyl, pyrazinyl, 1,3,5-triazinyl, indolyl, isoindolyl, indazolyl, benzimidazolyl, benzothiazolyl, quinolinyl, isoquinolinyl and pyrrolo[2,3-c]pyridinyl, optionally substituted with one or two substituents; or Ar represents a pyridinyl substituted with one or two substituents; the substituents being chosen from a halogen atom, $C_{1-6}$ alkyl, $C_{1-6}$ thioalkyl, $C_{1-6}$ alkoxy, $CH_2OH$, phenoxy, morpholinyl, —$CH_2$-morpholinyl, $NH_2$, $NHR_2$, $NR_2R_3$, $NHSO_2R_2$, CN, $SO_2R_2$, $SO_2NH_2$, $SO_2NHR_2$, COOH, $COOR_2$, $CONH_2$, $CONHNH_2$, $CONHR_2$, $CH_2NHR_2$ and $CH_2NR_2R_3$; and/or $R_2$ and $R_3$ represent, independently of each other, a $C_{1-6}$ alkyl optionally substituted with a group $CONH_2$, with a phenyl or with a heteroaromatic group; or $R_2$ and $R_3$ represent, independently of each other, a phenyl or a heteroaromatic group; and/or n represents 0, 1, 2 or 3;

when $R_1$ represents a halogen atom, $NH_2$, $NHR_2$, $NHCOR_2$, $NO_2$, CN, $CH_2NH_2$ or $CH_2NHR_2$;

or alternatively $R_1$ represents a phenyl optionally substituted with one or two substituents chosen from a halogen atom, hydroxyl, $C_{1-6}$ alkyl, $C_{1-6}$ alkoxy, $NH_2$, $NHR_2$ and $NR_2R_3$;

or alternatively $R_1$ represents a heteroaromatic group optionally substituted with one or two substituents chosen from a halogen atom, hydroxyl, a heteroaromatic group, $C_{1-6}$ alkyl, $NH_2$, $NHR_2$, $NHCOR_2$, $COOR_2$, $CONH_2$, $CONHR_2$ and $CH_2XR_2$ where X represents an atom chosen from O, N and S;

then Ar represents a phenyl group optionally substituted with one or two substituents chosen from a bromine or iodine atom, $C_{2-6}$ alkyl, $C_{2-6}$ thioalkyl, $C_{2-6}$ alkoxy, $CH_2OH$, phenoxy, morpholinyl, —$CH_2$-morpholinyl, $NH_2$, $NHR_2$, $NR_2R_3$, $NHSO_2R_2$, CN, $SO_2R_2$, $SO_2NH_2$, $SO_2NHR_2$, COOH, $COOR_2$, $CONH_2$, $CONHNH_2$, $CONHR_2$, $CH_2NHR_2$ and $CH_2NR_2R_3$;

or alternatively Ar represents a heteroaromatic group, optionally substituted with one or two substituents chosen from a halogen atom, $C_{1-6}$ alkyl, $C_{1-6}$ thioalkyl, $C_{1-6}$ alkoxy, $CH_2OH$, phenoxy, morpholinyl, —$CH_2$-morpholinyl, $NH_2$, $NHR_2$, $NR_2R_3$, $NHSO_2R_2$, CN, $SO_2R_2$, $SO_2NH_2$, $SO_2NHR_2$, COOH, $COOR_2$, $CONH_2$, $CONHNH_2$, $CONHR_2$, $CH_2NHR_2$ and $CH_2NR_2R_3$; and/or $R_2$ and $R_3$ represent, independently of each other, a $C_{1-6}$ alkyl optionally substituted with a group $CONH_2$, with a phenyl or with a heteroaromatic group; or $R_2$ and $R_3$ represent, independently of each other, a phenyl or a heteroaromatic group; and/or n represents 0, 1, 2 or 3.

Among the compounds of general formula (I), a third family of preferred compounds consists of the compounds for which:

when $R_1$ represents a hydrogen atom, then Ar represents a phenyl substituted with one or two substituents chosen from a bromine atom, $CH_2OH$, phenoxy, $NH_2$, $NHR_2$, $NR_2R_3$, CN, $SO_2NH_2$, COOH, $COOR_2$ and $CONH_2$;

or alternatively Ar represents a heteroaromatic group chosen from imidazolyl, 1,3,4-thiadiazolyl, pyrazinyl, indolyl, indazolyl, quinolinyl and isoquinolinyl, optionally substituted with one or two substituents; or Ar represents a pyridinyl substituted with one or two substituents; the substituents being chosen from a halogen atom, more particularly a chlorine, a COOH, a $C_{1-6}$ alkyl, more particularly a methyl, a $C_{1-6}$ alkoxy, more particularly a methoxy; and/or $R_2$ and $R_3$ represent, independently of each other, a $C_{1-6}$ alkyl, more particularly a methyl or an ethyl; or $R_2$ and $R_3$ represent, independently of each other, a phenyl; and/or n represents 0, 2 or 3;

when $R_1$ represents a halogen atom, more particularly a bromine or an iodine, $NH_2$, $NHCOR_2$, $NO_2$, CN or $CH_2NH_2$;

or alternatively $R_1$ represents a phenyl;

or alternatively $R_1$ represents a heteroaromatic group, more particularly pyrazolyl, tetrazolyl, thiazolyl, oxazolyl, pyridinyl, pyrimidinyl, quinolinyl, isoquinolinyl or pyrrolo[2,3-c]pyridinyl, optionally substituted with one or two substituents chosen from a halogen atom, more particularly a chlorine or a fluorine, a hydroxyl, a heteroaromatic group, more particularly a pyridinyl, a $C_{1-6}$ alkyl, more particularly a methyl, $NH_2$, $NHR_2$, $NHCOR_2$, $COOR_2$, $CONH_2$, $CONHR_2$ and $CH_2OR_2$;

then Ar represents a phenyl optionally substituted with one or two substituents chosen from a halogen atom, more particularly a chlorine or a fluorine, morpholinyl, —$CH_2$-morpholinyl, $NHSO_2R_2$, CN, $SO_2R_2$, $SO_2NH_2$, $SO_2NHR_2$, COOH, $CONHNH_2$, $CH_2NHR_2$ and $CH_2NR_2R_3$;

or alternatively Ar represents a heteroaromatic group, more particularly a pyridinyl, optionally substituted with a $C_{1-6}$ alkoxy, preferably a methoxy; and/or $R_2$ and $R_3$ represent, independently of each other, a $C_{1-6}$ alkyl, more particularly a methyl, an ethyl or a 2-methylpropyl, optionally substituted with a group $CONH_2$ or with a phenyl; or $R_2$ and $R_3$ represent, independently of each other, a phenyl or a heteroaromatic group, more particularly a pyridinyl or a pyrimidinyl; and/or n represents 0 or 1.

Among the compounds of general formula (I), a fourth family of particularly preferred compounds consists of the compounds for which:

$R_1$ represents a heteroaromatic group optionally substituted with one or two substituents chosen from a halogen atom, a hydroxyl, a heteroaromatic group, $C_{1-6}$ alkyl, $NH_2$, $NHR_2$, $NHCOR_2$, $COOR_2$, $CONH_2$, $CONHR_2$ and $CH_2XR_2$ where X represents an atom chosen from O, N and S; and/or Ar represents a phenyl group optionally substituted with one or two substituents chosen from a halogen atom, $C_{1-6}$ alkyl, $C_{1-6}$ thioalkyl, $C_{1-6}$ alkoxy, $CH_2OH$, phenoxy, morpholinyl, —$CH_2$-morpholinyl, $NH_2$, $NHR_2$, $NR_2R_3$, $NHSO_2R_2$, CN, $SO_2R_2$, $SO_2NH_2$, $SO_2NHR_2$, COOH, $COOR_2$, $CONH_2$, $CONHNH_2$, $CONHR_2$, $CH_2NHR_2$ and $CH_2NR_2R_3$;

or alternatively Ar represents a heteroaromatic group, optionally substituted with one or two substituents chosen from a halogen atom, $C_{1-6}$ alkyl, $C_{1-6}$ thioalkyl, $C_{1-6}$ alkoxy, $CH_2OH$, phenoxy, morpholinyl, —$CH_2$-morpholinyl, $NH_2$, $NHR_2$, $NR_2R_3$, $NHSO_2R_2$, CN, $SO_2R_2$, $SO_2NH_2$, $SO_2NHR_2$, COOH, $COOR_2$, $CONH_2$, $CONHNH_2$, $CONHR_2$, $CH_2NHR_2$ and $CH_2NR_2R_3$; and/or $R_2$ and $R_3$ represent, independently of each other, a $C_{1-6}$ alkyl optionally substituted with a group $CONH_2$, with a phenyl or with a heteroaromatic group; or $R_2$ and $R_3$ represent, independently of each other, a phenyl or a heteroaromatic group; and/or n represents 0, 1, 2 or 3.

Among the compounds of general formula (I), a fifth family of particularly preferred compounds consists of the compounds for which:

$R_1$ represents a heteroaromatic group, more particularly pyrazolyl, thiazolyl, oxazolyl, pyridinyl, isoquinolinyl or pyrrolo[2,3-c]pyridinyl, optionally substituted with one or two substituents chosen from a halogen atom, more particularly a chlorine, a heteroaromatic group, more particularly a pyridinyl, a $C_{1-6}$ alkyl, more particularly a methyl, $NH_2$ and $CONHR_2$; and/or Ar represents a phenyl optionally substituted with one or two substituents chosen from morpholinyl, —$CH_2$-morpholinyl, $NHSO_2R_2$, CN, $SO_2R_2$, $SO_2NH_2$, $SO_2NHR_2$, COOH, $CH_2NHR_2$ and $CH_2NR_2R_3$;

or alternatively Ar represents a heteroaromatic group, more particularly a pyridinyl, optionally substituted with a $C_{1-6}$ alkoxy, preferably a methoxy; and/or $R_2$ and $R_3$ represent, independently of each other, a $C_{1-6}$ alkyl, more particularly a methyl or an ethyl, optionally substituted with a group $CONH_2$, or with a phenyl;

or $R_2$ and $R_3$ represent, independently of each other, a heteroaromatic group, more particularly a pyridinyl or a pyrimidinyl; and/or n represents 0 or 1.

By way of example of preferred compounds of general formula (I), the following compounds may be mentioned:

—N-(pyridin-4-yl)-5-pyridin-3-yl-1H-indazole-3-carboxamide hydrochloride
—N-(pyridin-4-yl)-5-(4-methyl-[3,4']bipyridinyl-5-yl)-1H-indazole-3-carboxamide hydrochloride
—N-(pyridin-4-yl)-5-isoquinolin-4-yl-1H-indazole-3-carboxamide
—N-(pyridin-3-ylmethyl)-5-isoquinolin-4-yl-1H-indazole-3-carboxamide
—N-(3-cyanophenyl)-5-isoquinolin-4-yl-1H-indazole-3-carboxamide
—N-(4-sulphamoylphenyl)-5-isoquinolin-4-yl-1H-indazole-3-carboxamide
-4-[5-(isoquinolin-4-yl)-1H-indazole-3-carbonylamino]benzoic acid
—N-(pyridin-4-yl)-5-[4-methyl-5-(pyridin-3-ylcarbamoyl)pyridin-3-yl]-1H-indazole-3-carboxamide
—N-(pyridin-4-yl)-5-(4-methyl[3,3']bipyridinyl-5-yl)-1H-indazole-3-carboxamide
—N-{4-[(N-methylsulphonyl)amino]phenyl}-5-pyridin-3-yl-1H-indazole-3-carboxamide
—N-(pyridin-4-yl)-5-(1,3-thiazol-5-yl)-1H-indazole-3-carboxamide
—N-(pyridin-4-yl)-5-(1H-pyrrolo[2,3-c]pyridin-4-yl)-1H-indazole-3-carboxamide
-5-(1H-pyrazol-4-yl)-N-(pyridin-4-yl)-1H-indazole-3-carboxamide
—N-(pyridin-4-yl)-5-[(2-chloro)pyridin-5-yl]-1H-indazole-3-carboxamide
-5-(1,3-oxazol-5-yl)-N-(pyridin-4-yl)-1H-indazole-3-carboxamide
—N-{3-[(ethylamino)methyl]phenyl}-5-isoquinolin-4-yl-1H-indazole-3-carboxamide dihydrochloride
-5-(5-amino-4-methylpyridin-3-yl)-N-(pyridin-4-yl)-1H-indazole-3-carboxamide
—N-(pyridin-4-yl)-5-(3-(N-aminoketomethyl)carboxamide)pyridin-4-yl-1H-indazole-3-carboxamide
—N-(pyridin-3-ylmethyl)-5-(1,3-thiazol-5-yl)-1H-indazole-3-carboxamide
—N-(pyridin-3-ylmethyl)-5-pyridin-3-yl-1H-indazole-3-carboxamide
—N-(4-sulphamoylphenyl)-5-pyridin-3-yl-1H-indazole-3-carboxamide
—N-(3-sulphamoylphenyl)-5-pyridin-3-yl-1H-indazole-3-carboxamide
—N-phenyl-5-pyridin-3-yl-1H-indazole-3-carboxamide
—N-(3-methylsulphonamidophenyl)-5-pyridin-3-yl-1H-indazole-3-carboxamide
—N-(4-morpholin-4-ylphenyl)-5-pyridin-3-yl-1H-indazole-3-carboxamide
-5-pyridin-3-yl-N-{4-[(N-pyrimidin-2-ylamino)sulphonyl]phenyl}-1H-indazole-3-carboxamide
—N-(4-methylsulphonylphenyl)-5-pyridin-3-yl-1H-indazole-3-carboxamide
-5-(4-hydroxy-3-methylpyridin-2-yl)-N-pyridin-4-yl-1H-indazole-3-carboxamide
—N-(3-cyanophenyl)-5-oxazol-5-yl-1H-indazole-3-carboxamide
—N-(2-methoxypyridin-5-yl)-5-(1,3-oxazol-5-yl)-1H-indazole-3-carboxamide
—N-{3-[(ethylamino)methyl]phenyl}-5-(1,3-thiazol-5-yl)-1H-indazole-3-carboxamide
—N-{3-[(diethylamino)methyl]phenyl}-5-(1,3-oxazol-5-yl)-1H-indazole-3-carboxamide
—N-{3-[(diethylamino)methyl]phenyl}-5-(1,3-thiazol-5-yl)-1H-indazole-3-carboxamide
—N-[3-(morpholin-4-ylmethyl)phenyl]-5-pyridin-3-yl-1H-indazole-3-carboxamide
—N-(3,5-difluorobenzyl)-5-pyridin-3-yl-1H-indazole-3-carboxamide
—N-(3,4-difluorobenzyl)-5-pyridin-3-yl-1H-indazole-3-carboxamide The subject of the invention is also, among the compounds of general formula (I), compounds corresponding to general formula (I'):

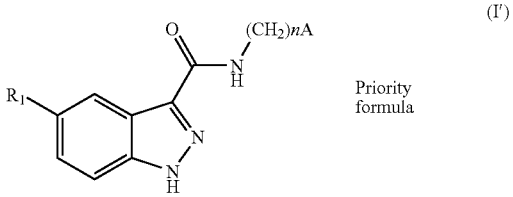

Priority formula in which, $R_1$ represents a hydrogen or halogen atom, $NH_2$, $NHR_2$, $NHCOR_2$, $NO_2$, CN, $CH_2NH_2$ or $CH_2NHR_2$;

or alternatively $R_1$ represents a phenyl optionally substituted with one or two substituents chosen from a halogen atom, a hydroxyl, $C_{1-6}$ alkyl, $C_{1-6}$ alkoxy, $NH_2$, $NHR_2$ and $NR_2R_3$;

or alternatively $R_1$ represents a heteroaromatic optionally substituted with one or more substituents chosen from a heteroaromatic, $C_{1-6}$ alkyl, $NH_2$, $NHR_2$, $NHCOR_2$, $CONH_2$, $CONHR_2$ and $CH_2XR_2$ where X represents an atom chosen from O, NH and S;

Ar represents a phenyl group optionally substituted with one or two substituents chosen from a halogen atom, $C_{1-6}$ alkyl, $C_{1-6}$ thioalkyl, $C_{1-6}$ alkoxy, $CH_2OH$, phenoxy, $NH_2$, $NHR_2$, $NR_2R_3$, CN, $SO_2NH_2$, $SO_2NHR_2$, COOH, $COOR_2$, $CONH_2$ and $CONHR_2$;

or alternatively Ar represents a heteroaromatic, optionally substituted with one or two substituents chosen from a halogen atom, COOH, $C_{1-6}$ alkyl, $C_{1-6}$ alkoxy;

$R_2$ and $R_3$ represent, independently of each other, a $C_{1-6}$ alkyl optionally substituted with a phenyl or a heteroaromatic; or $R_2$ and $R_3$ represent, independently of each other, a phenyl or a heteroaromatic;

n represents 0, 1, 2 or 3.

The following compounds do not form part of the compounds corresponding to general formula (I'):

—N-phenyl-1H-indazole-3-carboxamide;
—N-(2-chlorophenyl)-1H-indazole-3-carboxamide;
—N-(3-chlorophenyl)-1H-indazole-3-carboxamide;
—N-(4-chlorophenyl)-1H-indazole-3-carboxamide;
—N-(2,4-dichlorophenyl)-1H-indazole-3-carboxamide;
—N-(3,4-dichlorophenyl)-1H-indazole-3-carboxamide;
—N-(2-methylphenyl)-1H-indazole-3-carboxamide;
—N-(2-methoxyphenyl)-1H-indazole-3-carboxamide;
—N-(4-methoxyphenyl)-1H-indazole-3-carboxamide;
—N-(4-thiomethylphenyl)-1H-indazole-3-carboxamide;
—N-(3-chloro-4-thiomethylphenyl)-5-amino-1H-indazole-3-carboxamide;
—N-benzyl-1H-indazole-3-carboxamide;
—N-(2-chlorobenzyl)-1H-indazole-3-carboxamide;
—N-(4-methylbenzyl)-1H-indazole-3-carboxamide;
—N-(pyridin-2-ylmethyl)-1H-indazole-3-carboxamide;
—N-(pyridin-3-ylmethyl)-1H-indazole-3-carboxamide;
—N-(pyridin-4-ylmethyl)-1H-indazole-3-carboxamide;
—N-(2-phenylethyl)-1H-indazole-3-carboxamide;
—N-(3,4-dimethoxyphenylethyl)-1H-indazole-3-carboxamide;
—N-[3-(pyridin-2-yl)propyl]-1H-indazole-3-carboxamide;
—N-[3-(2,6-dimethylphenyl)propyl]-5-nitro-1H-indazole-3-carboxamide.

Among the compounds of general formula (I'), a first family of preferred compounds consists of the compounds for which:

$R_1$ represents a hydrogen or halogen atom, $NH_2$, $NHR_2$, $NHCOR_2$, $NO_2$, CN, $CH_2NH_2$ or $CH_2NHR_2$;

or alternatively $R_1$ represents a phenyl optionally substituted with one or two substituents chosen from a halogen atom, hydroxyl, $C_{1-4}$ alkyl, $C_{1-6}$ alkoxy, $NH_2$, $NHR_2$ and $NR_2R_3$;

or alternatively $R_1$ represents a heteroaromatic optionally substituted with one or more substituents chosen from a heteroaromatic, $C_{1-6}$ alkyl, $NH_2$, $NHR_2$, $NHCOR_2$, $CONH_2$, $CONHR_2$ and $CH_2XR_2$, where X represents an atom chosen from O, NH and S; and/or Ar represents a phenyl optionally substituted with one or two substituents chosen from a halogen atom, $C_{1-6}$ alkyl, $C_{1-6}$ thioalkyl, $C_{1-6}$ alkoxy, $CH_2OH$, phenoxy, $NH_2$, $NHR_2$, $NR_2R_3$, CN, $SO_2NH_2$, $SO_2NHR_2$, COOH, $COOR_2$, $CONH_2$ and $CONHR_2$;

or alternatively Ar represents a heteroaromatic, optionally chosen from one or two substituents chosen from a halogen atom, a COOH, a $C_{1-6}$ alkyl, a $C_{1-6}$ alkoxy; and/or $R_2$ and $R_3$ represent, independently of each other, a $C_{1-6}$ alkyl optionally substituted with a phenyl or a heteroaromatic or $R_2$ represents a phenyl or a heteroaromatic; and/or n represents 0, 1, 2 or 3;

with the condition that when $R_1$ represents a hydrogen atom if n represents 0 and Ar is a phenyl, then the phenyl is necessarily substituted as defined above, the methyl, methoxy, thiomethyl and chlorine atom substituents being excluded;

if n represents 1, and then Ar is a phenyl, then the phenyl is necessarily substituted as defined above, the methyl and chlorine atom substituents being excluded;

if n represents 1, and then Ar is a pyridinyl, then the pyridinyl is necessarily substituted as defined above;

if n represents 2 and Ar is a phenyl, then the phenyl is necessarily substituted as defined above, the methoxy substituent being excluded;

if n represents 3 and Ar is a pyridinyl, then the pyridinyl is necessarily substituted as defined above;

when $R_1$ represents an $NH_2$ if n represents 0 and Ar is a phenyl, then the substituent(s) of the phenyl cannot be chosen from a thiomethyl or a chlorine atom;

when $R_1$ represents an $NO_2$ if n represents 3 and Ar is a phenyl, then the substituent(s) of the phenyl of Ar cannot be a methyl.

Among the compounds of general formula (I'), a second family of preferred compounds consists of the compounds for which:

when $R_1$ represents a hydrogen atom, then Ar represents a phenyl substituted with one or two substituents chosen from a bromine or iodine atom, $C_{2-6}$ alkyl, $C_{2-6}$ thioalkyl, $C_{2-6}$ alkoxy, $CH_2OH$, phenoxy, $NH_2$, $NHR_2$, $NR_2R_3$, CN, $SO_2NH_2$, $SO_2NHR_2$, COOH, $COOR_2$, $CONH_2$ and $CONHR_2$;

or alternatively Ar represents a heteroaromatic chosen from pyrrolyl, imidazolyl, pyrazolyl, isothiazolyl, 1,3,4-thiadiazolyl, pyridazinyl, pyrimidinyl, pyrazinyl, indolyl, indazolyl, quinolinyl and isoquinolinyl, optionally substituted with one or two substituents; or Ar represents a pyridinyl substituted with one or two substituents; the substituents being chosen from a halogen atom, a COOH, $C_{1-6}$ alkyl, $C_{1-6}$ alkoxy; and/or $R_2$ and $R_3$ represent, independently of each other, a $C_{1-6}$ alkyl optionally substituted with a phenyl or a heteroaromatic; or $R_2$ and $R_3$ represent, independently of each other, a phenyl or a heteroaromatic; and/or n represents 0, 1, 2 or 3;

when $R_1$ represents a halogen atom, $NH_2$, $NHR_2$, $NHCOR_2$, $NO_2$, CN, $CH_2NH_2$ or $CH_2NHR_2$;

or alternatively $R_1$ represents a phenyl optionally substituted with one or two substituents chosen from a halogen atom, hydroxyl, $C_{1-6}$ alkyl, $C_{1-6}$ alkoxy, $NH_2$, $NHR_2$ and $NR_2R_3$;

or alternatively $R_1$ represents a heteroaromatic optionally substituted with one or more substituents chosen from a heteroaromatic, $C_{1-6}$ alkyl, $NH_2$, $NHR_2$, $NHCOR_2$, $CONH_2$, $CONHR_2$ and $CH_2XR_2$, where X represents an atom chosen from O, NH and S;

then Ar represents a phenyl optionally substituted with one or two substituents chosen from a bromine or iodine atom, $C_{2-6}$ alkyl, $C_{2-6}$ thioalkyl, $C_{1-6}$ alkoxy, $CH_2OH$, phenoxy, $NH_2$, $NHR_2$, $NR_2R_3$, CN, $SO_2NH_2$, $SO_2NHR_2$, COOH, $COOR_2$, $CONH_2$ and $CONHR_2$;

or alternatively Ar represents a heteroaromatic, optionally substituted with one or two substituents chosen from a halogen atom, a COOH, a $C_{1-6}$ alkyl and a $C_{1-6}$ alkoxy; and/or $R_2$ and $R_3$ represent, independently of each other, a $C_{1-6}$ alkyl optionally substituted with a phenyl or a heteroaromatic; or $R_2$ and $R_3$ represent, independently of each other, a phenyl or a heteroaromatic; and/or n represents 0, 1, 2 or 3.

In the context of the invention, there is understood by:

$C_{t-z}$ where t and z may take the values from 1 to 6, a carbon chain which may have from t to z carbon atoms, for example $C_{1-6}$ a carbon chain which may have from 1 to 6 carbon atoms;

alkyl, a linear or branched, saturated aliphatic group; for example, a $C_{1-6}$ alkyl group represents a linear or branched carbon chain of 1 to 6 carbon atoms, more particularly methyl, ethyl, propyl, isopropyl, butyl, isobutyl, sec-butyl, tert-butyl or pentyl, and the like;

alkoxy, an alkyloxy group having a linear or branched, saturated aliphatic chain;

thioalkyl, an —S-alkyl group having a linear or branched, saturated aliphatic chain;

a halogen atom, a fluorine, chlorine, bromine or iodine;

a heteroaromatic group: a cyclic aromatic group comprising between 5 and 9 carbon atoms and comprising between 1 and 4 heteroatoms, such as nitrogen, oxygen or sulphur. By way of examples of heteroaromatic groups, there may be mentioned the pyrrolyl, imidazolyl, pyrazolyl, triazolyl, tetrazolyl, thiazolyl, isothiazolyl, 1,3,4-thiadiazolyl, oxazolyl, isoxazolyl, oxadiazolyl, pyridinyl, pyridazinyl, pirimidinyl, pyrazinyl, 1,3,5-triazinyl, indolyl, isoindolyl, indazolyl, benzimidazolyl, benzothiazolyl, quinolinyl, isoquinolinyl and pyrrolo[2,3-c]pyridinyl groups.

The compounds of general formula (I) may comprise one or more asymmetric carbon atoms. They may therefore exist in the form of enantiomers or diastereoisomers. These enantiomers, diastereoisomers and mixtures thereof, including the racemic mixtures, form part of the invention.

The compounds of general formula (I) may exist in the form of tautomers. Thus, the subject of the invention is the compounds of the invention in all their tautomeric forms.

The compounds of general formula (I) may exist in the form of bases or addition salts with acids. Such addition salts form part of the invention. These salts are advantageously prepared with pharmaceutically acceptable acids, but the salts of other acids useful, for example, for the purification or isolation of the compounds of general formula (I) also form part of the invention.

The compounds of general formula (I) may exist in the form of hydrates or solvates, namely in the form of associations or combinations with one or more molecules of water or with a solvent. Such hydrates and solvates also form part of the invention.

The subject of the present invention is also methods for preparing the compounds of general formula (I).

Thus, the compounds of the invention may be prepared by the methods illustrated in the schemes which follow, of which the operating conditions are standard for persons skilled in the art.

The expression protecting group PG is understood to mean a group which makes it possible to prevent the reactivity of a functional group or a position, during a chemical reaction capable of affecting it, and which restores the molecule after cleavage according to methods known to persons skilled in the art. Examples of protecting groups and methods of protection and deprotection are given, inter alia, in Protective groups in Organic Synthesis, Green et al., 2nd Ed. (John Wiley & Sons, Inc., New York).

When $R_1$ represents a halogen atom, $NO_2$ or CN, the compounds of general formula (I) may be prepared by the method illustrated in scheme 1. This method consists in converting an indole of general formula (II), where $R_1$ is $NO_2$, CN or a halogen atom, to an indazole-3-carbaldehyde of general formula (III) for example with nitrous acid. The compound of general formula (III) is then protected in a basic medium with a group PG, of the trimethylsilylethoxymethyl (SEM) or mesitylenesulphonyl (Mts) type, to give indazole-3-carbaldehyde protected at the 1-position of general formula (IV). The compound (IV) is oxidized to indazole-3-carboxylic acid of general formula (V), for example by reaction with sodium chlorite. Indazole-3-carboxamide protected at the 1-position of general formula (VII) is obtained by coupling the compound of general formula (V) with an amine of general formula $Ar(CH_2)nNH_2$ (VI) in which Ar and n are as defined in general formula (I). This coupling reaction may be carried out by activating a compound of general formula (V) with coupling reagents, such as carbonyldiimidazole or isopropyl or isobutyl chloroformate. The deprotection of the compound of general formula (VII) may be carried out either by the action of a base such as sodium hydroxide, or in the presence of tetrabutylammonium fluoride (TBAF) and ethylenediamine, or alternatively in the presence of trifluoroacetic acid and then heating with ethylenediamine. This deprotection step makes it possible to obtain the indazole-3-carboxamide of general formula (I). In the case where $R_1$ is a hydrogen atom, the method of preparation described in scheme 1 is repeated, carrying out the reaction of coupling of the amine of general formula $Ar(CH_2)nNH_2$ (VI), as defined above, with commercial indazole-3-carboxylic acid.

The compounds of general formula (I), where $R_1$ represents $NH_2$, are obtained by reducing a compound of general formula (I), where $R_1$ is $NO_2$, as obtained in scheme 1, for example in the presence of tin chloride.

The compounds of general formula (I), where $R_1$ represents $NHR_2$ or $NHCOR_2$, are obtained by functionalization of the corresponding compounds of general formula (I), where $R_1$ is $NH_2$, according to techniques known to persons skilled in the art.

The compounds of general formula (I), where $R_1$ represents $CH_2NH_2$, are obtained by hydrogenation at atmospheric pressure of a compound of general formula (I), where $R_1$ is CN, as obtained according to scheme 1, for example in the presence of palladium on carbon.

The compounds of general formula (I), where $R_1$ represents $CH_2NHR_2$, are obtained by functionalization of the corresponding compounds of general formula (I), where $R_1$ is $CH_2NH_2$, according to techniques known to persons skilled in the art.

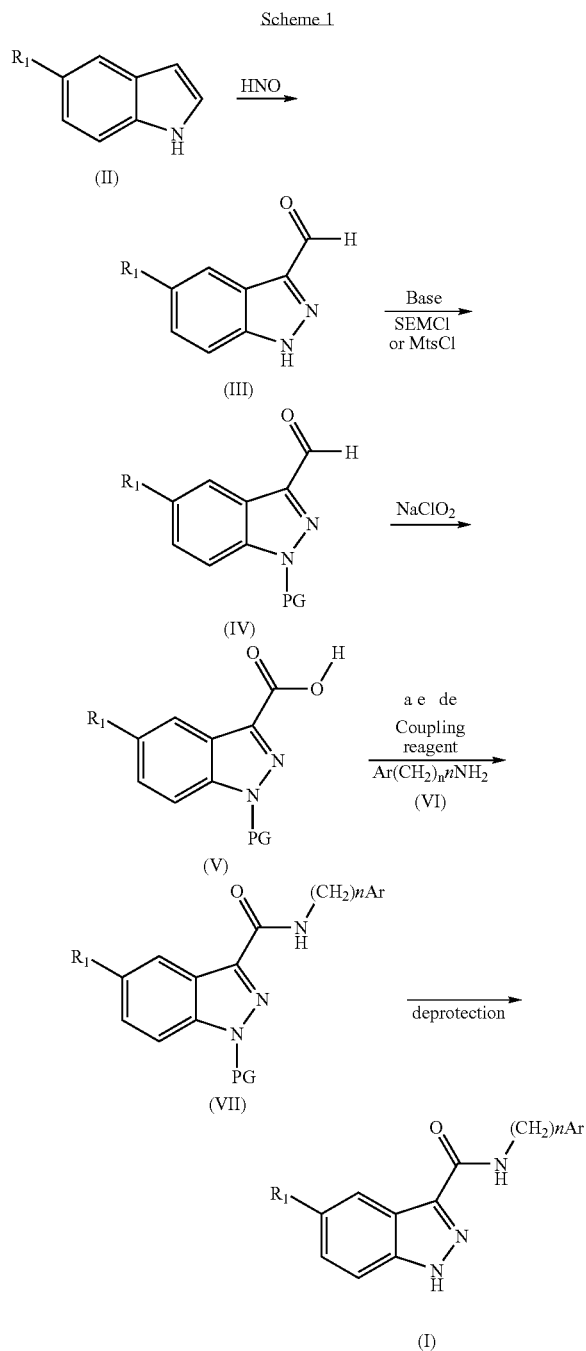

When $R_1$ represents an optionally substituted phenyl or heteroaromatic group, the compounds of general formula (I) may be obtained according to one of the methods illustrated in schemes 1, 2 and 3. However, when $R_1$ represents an oxazolyl group, the compounds of formula (I) may be obtained according to scheme 4 and when $R_1$ represents a thiazolyl group, compounds of formula (I) may be obtained according to scheme 5.

In the case of scheme 1, the compound of general formula (II), where $R_1$ represents an optionally substituted phenyl or heteroaromatic group as defined in general formula (I), may be obtained for example by a Suzuki type reaction on 5-iodoindole according to techniques known to persons skilled in the art.

Scheme 2 illustrates an alternative method of preparation of the compound of general formula (VII) from 5-iodoindole.

The compound of general formula (IVa), where SEM is a trimethylsilylethoxymethyl group, is obtained by repeating the first two steps illustrated in scheme 1. A Suzuki reaction, carried out for example in the presence of a boronic acid of general formula $R_1B(OH)_2$ (VIII), where $R_1$ represents an optionally substituted phenyl or heteroaromatic group as defined in general formula (I), of an inorganic base, such as sodium carbonate ($Na_2CO_3$), and palladium(0), makes it possible to obtain the compound of general formula (IV) in which PG represents an SEM group. The compound of general formula (I), where $R_1$ represents an optionally substituted phenyl or heteroaromatic group as defined in general formula (I), is obtained from the compound of general formula (IV) by repeating the last three steps illustrated in scheme 1.

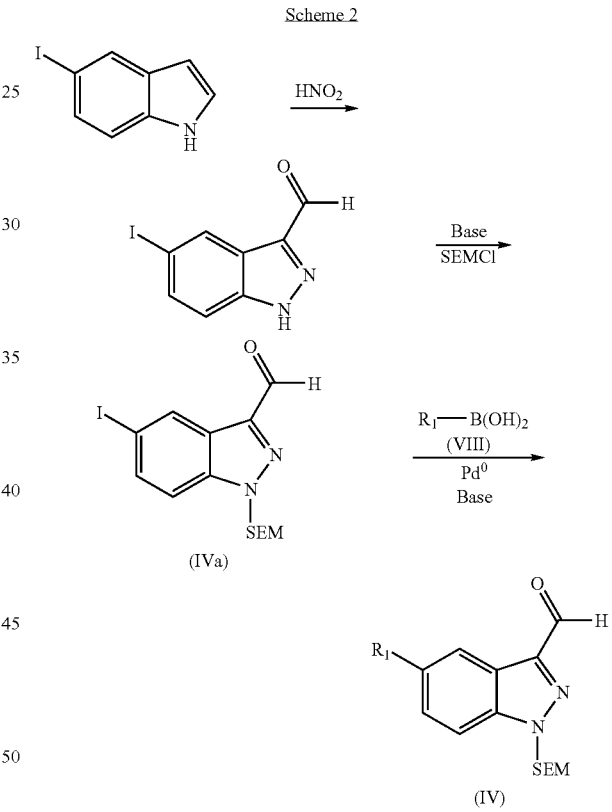

Scheme 3 illustrates a method of preparation from 5-iodo- or 5-bromoisatin.

5-Iodo- or 5-bromoindazolecarboxylic acid may be obtained by opening the indoledione ring of 5-iodo- or 5-bromoisatin, for example in the presence of sodium hydroxide, followed by diazotization, for example using nitrous acid, and finally by reduction and formation of the indazole ring, for example in the presence of tin chloride ($SnCl_2$). The 5-iodo- or 5-bromoindazole-3-carboxylic acid obtained is then protected in basic medium, for example with an SEM group, to give the compound of general formula (IX), in which X represents a bromine or iodine atom.

The indazole-3-carboxamide of general formula (X) may be obtained by coupling the compound of general formula (IX) with an amine of general formula Ar(CH$_2$)nNH$_2$ (VI), in which Ar and n are as defined in general formula (I). This coupling reaction may be carried out by activating a compound of general formula (IX) with coupling reagents such as carbonyldiimidazole or isopropyl or isobutyl chloroformate.

optionally substituted phenyl or heteroaromatic group as defined in general formula (I) and X is a bromine or iodine atom.

The compound of general formula (I), where R$_1$ represents an optionally substituted phenyl or heteroaromatic group as

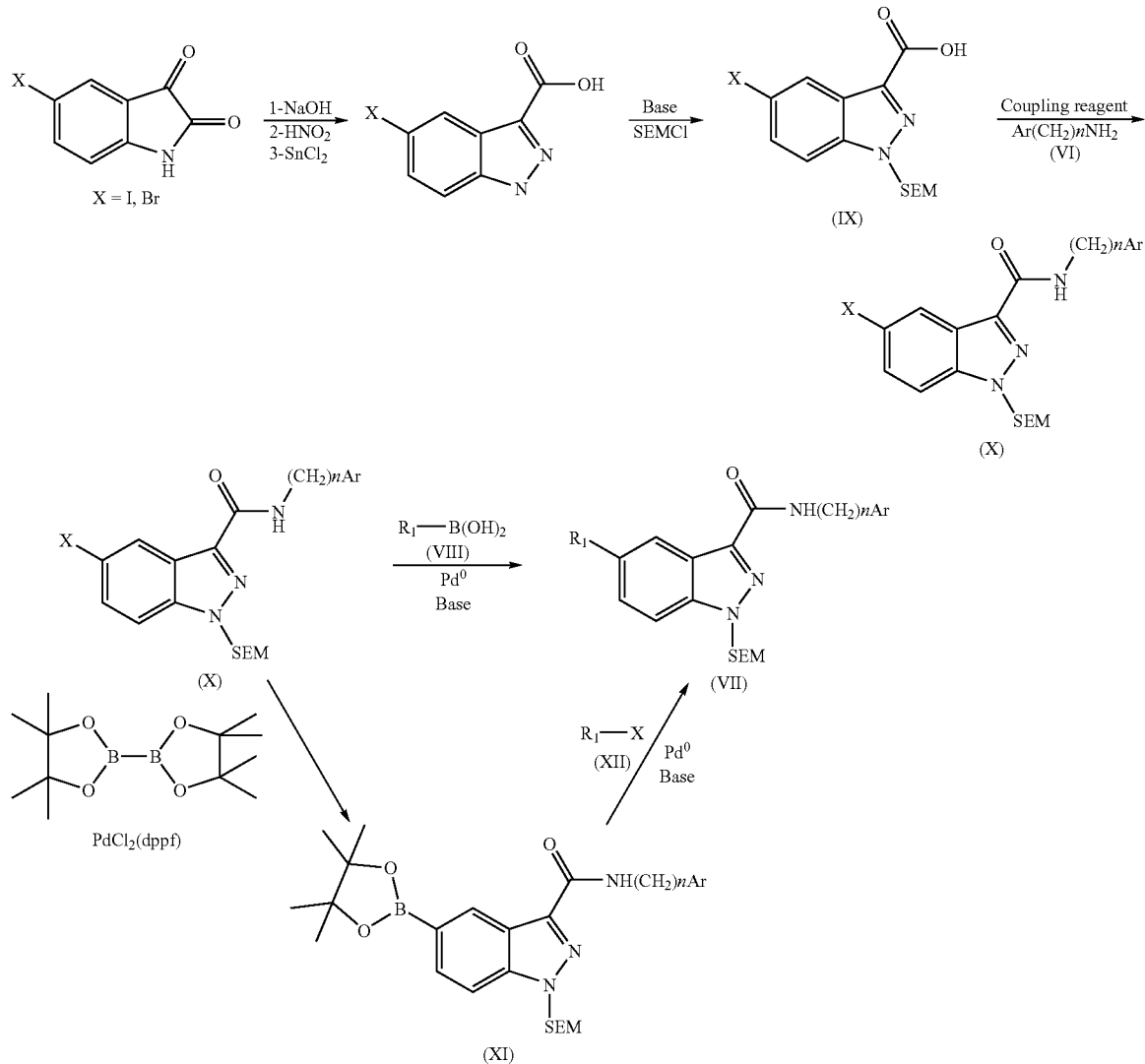

Scheme 3 defined in general formula (I), is obtained by deprotecting the compound of general formula (VII), as illustrated in the last step of scheme 1.

Scheme 4 illustrates a method of preparing the compounds of general formula (VIIa), that is to say the compounds of general formula (VII) for which R$_1$ represents an oxazolyl group and PG represents an SEM group. The compound of general formula (X), as defined above and in which X represents an iodine atom, is formylated for example in the presence of carbon monoxide and of a palladium complex, such as tetrakis(triphenylphosphine)palladium, and then of a reducing agent, such as tributyltin hydride in a solvent such as tetrahydrofuran (THF). The compound of general formula (XIII) thus obtained is heated under reflux in a solvent, such as methanol, in the presence of tosylmethyl isocyanate The compound of general formula (VII) may be obtained from the compound of general formula (X) by 2 methods:
either by a Suzuki reaction, carried out in the presence of a boronic acid of general formula R$_1$B(OH)$_2$ (VIII), where R$_1$ represents an optionally substituted phenyl or heteroaromatic group as defined in general formula (I), of a base and of palladium(0);
or by means of a dioxaborolane of general formula (XI) obtained by the reaction of bis(pinacolato)diborane and of 1,1'-bis(diphenylphosphino)ferrocenedichloropalladiumII with the compound of general formula (X); the intermediate of general formula (XI) then being brought into contact with an inorganic base such as sodium or potassium acetate, of palladium(0) and of a compound of general formula R$_1$—X (XII), where R$_1$ represents an (TosMIC) and a base such as potassium carbonate (K$_2$CO$_3$), to give the compound of general formula (VIIa).

The compound of general formula (I), where R$_1$ represents an oxazolyl group, is obtained from the compound of general formula (VIIa) by deprotection as illustrated in the last step of scheme 1.

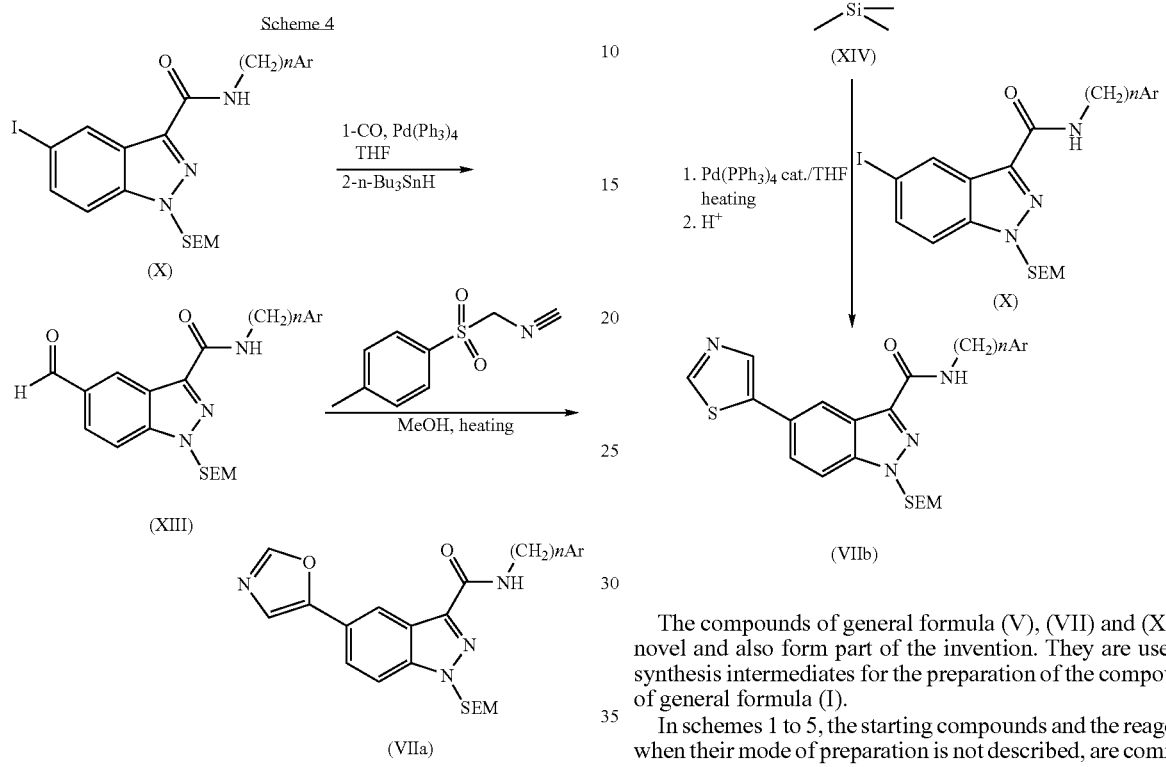

Scheme 5 illustrates a method of preparing the compounds of general formula (VIIb), that is to say the compounds of general formula (VII) for which R$_1$ represents a thiazolyl group and PG represents an SEM group. The thiazolyl group is introduced by heating the compound of general formula (X), as defined above and in which X represents an iodine atom, in the presence of the derivative of formula (XIV) illustrated in scheme 5, of tetrakis(triphenylphosphine)palladium in anhydrous THF and then by acidification. The derivative of formula (XIV) is prepared from 2-trimethylsilyl(thiazole), in the presence of a strong base, such as butyllithium, by the reaction of zinc chloride (ZnCl$_2$) in solution in anhydrous ether. The compound of general formula (VIIb) thus obtained is deprotected according to the last step of scheme 1 in order to obtain the compound of general formula (I), where R$_1$ represents a thiazolyl group.

Scheme 5

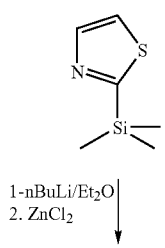

The compounds of general formula (V), (VII) and (X) are novel and also form part of the invention. They are used as synthesis intermediates for the preparation of the compounds of general formula (I).

In schemes 1 to 5, the starting compounds and the reagents, when their mode of preparation is not described, are commercially available or are described in the literature, or may be prepared by methods which are described therein or which are known to persons skilled in the art.

The following examples describe the preparation of some compounds in accordance with the invention. These examples are not limiting and only illustrate the invention.

The numbers for the compounds exemplified refer to those given in the table below. The microanalyses, the IR and NMR spectra and/or the LC/MS/UV (Liquid Chromatography coupled to Mass Spectroscopy and to Ultraviolet analysis) confirm the structures of the compounds obtained.

For each LC/MS/UV value provided, the percentage in brackets represents the UV purity of the compound.

EXAMPLE 1

Compound No. 1

N-(3-Imidazol-1-ylpropyl)-1H-indazole-3-carboxamide

Indazole-3-carboxylic acid (810 mg, 5 mmol) is heated at 60° C. in the presence of carbonyldiimidazole (891 mg, 5.5 mmol) in N,N-dimethylformamide (DMF) (14 ml) under argon for 3 h. 1-(3-Aminopropyl)-imidazole (597 μl, 5 mmol) in solution in DMF (2 ml) is added and the mixture is heated for 2 h and 20 min at 60° C. After cooling, the DMF is evaporated under vacuum to give a yellow oil which is chromatographed on 54 g of silica. The compound obtained is eluted with an ethyl acetate (AcOEt)/methanol (MeOH) (9/1) mixture.

690 mg of product are obtained.
m.p.: 154-155° C.
LC/MS/UV: MH+270 (100%)
$^1$H NMR (500 MHz, DMSO-D6) δ (ppm): 1.98 (quintuplet, 2H), 3.27 (m, 2H), 4.01 (t, 2H), 6.88 (s, 1H), 7.20 (s, 1H), 7.22 (m, 1H), 7.39 (m, 1H), 7.58 (m, 1H), 7.66 (s, 1H), 8.16 (m, 1H), 8.52 (m, 1H), 13.5 (s, 1H).

EXAMPLE 2

Compound No. 3

N-(4-Sulphamoylphenyl)-1H-indazole-3-carboxamide

A mixture of indazole-3-carboxylic acid (324 mg, 2 mmol), hydroxybenzotriazole (297 mg, 2.2 mmol) and diisopropylcarbodiimide (344 µl, 2.2 mmol) in DMF (10 ml) is stirred for 30 min at room temperature. Sulphanilamide (380 mg, 2.2 mmol) is added. The reaction mixture is stirred overnight at room temperature and then filtered. The filtrate is evaporated and is then extracted with AcOEt/H$_2$O. The organic phase is dried over MgSO$_4$, filtered and evaporated under vacuum to give a yellow solid (640 mg). This compound is recrystallized successively from AcOEt/CH$_2$Cl$_2$ and AcOEt/MeOH.

110 mg of product are obtained in the form of a cream-coloured solid.
m.p.: >250° C.
LC/MS/UV: MH+317 (96.5%)
$^1$H NMR (500 MHz, DMSO-D6) δ (ppm): 7.26 (s, 2H), 7.30 (m, 1H), 7.46 (m, 1H), 7.67 (m, 1H), 7.78 (d, 1H), 8.07 (d, 1H), 8.21 (d, 1H), 10.69 (s, 1H), 13.87 (s, 1H).

EXAMPLE 3

Compound No. 4

N-(4-Phenylaminophenyl)-1H-indazole-3-carboxamide

This compound is synthesized in a manner similar to the procedure described in Example 2 by coupling indazole-3-carboxylic acid and N-phenyl-1,4-phenylenediamine on the scale of 1 mmol, but using dicyclohexylcarbodiimide (DCC) as coupling reagent. The crude product obtained after extraction is taken up in CHCl$_3$. The insoluble matter is filtered and dried.

190 mg of product are obtained.
m.p.: 218° C.
LC/MS/UV: MH+329 (100%)
$^1$H NMR (500 MHz, DMSO-D6) δ (ppm): 6.76 (t, 1H), 7.02 (d, 2H), 7.06 (d, 2H), 7.19 (t, 2H), 7.27 (t, 1H), 7.44 (t, 1H), 7.64 (d, 1H), 7.74 (d, 2H), 8.04 (s, 1H), 8.21 (d, 1H), 10.14 (s, 1H), 13.65 (s, 1H).

EXAMPLE 4

Compound No. 6

N-(1H-Indazol-5-yl)-1H-indazole-3-carboxamide

Intermediate 4.1

1-(2,4,6-Trimethylbenzenesulphonyl)-1H-indazole-3-carboxylic acid

NaH (60% in oil, 40 mmol) is washed under argon with petroleum ether and then suspended in 60 ml of anhydrous DMF. An indazole-3-carboxylic acid solution (3.35 g, 20 mmol) in anhydrous DMF (50 ml) is added dropwise to this suspension kept at 0° C. The reaction mixture becomes clear. When the addition is complete, the medium is allowed to react for 30 min at room temperature and then the reaction mixture is again cooled to 0° C. Mesitylenesulphonyl chloride (4.82 g, 22 mmol) in solution in anhydrous tetrahydrofuran (THF) (50 ml) is added. The ice bath is removed and a suspension appears. The medium is allowed to react for 30 min at room temperature. The solvents are evaporated under vacuum and the residue is taken up in 0.1N NaOH solution. The solution obtained is washed with diethyl ether and then acidified with 6N HCl. The compound which separates is filtered, and taken up in AcOEt. The AcOEt solution is dried over Na$_2$SO$_4$ and then evaporated. The residue (6.18 g) is recrystallized from AcOEt/petroleum ether.

4.89 g of product are obtained in the form of a yellow solid.
m.p.: 208-209° C.

Intermediate 4.2

Isopropyl [1-(2,4,6-trimethylbenzenesulphonyl)-1H-indazol-3-yl]carbonylcarbonate An isopropyl chloroformate solution (1M in toluene, 22 ml) is added dropwise to a solution of intermediate 4.1 (7.58 g, 22 mmol) in 300 ml of anhydrous THF kept at 0° C. under argon, followed by N-methylmorpholine (2.42 ml, 22 mmol). A precipitate appears, the stirring is maintained for 15 min at 0° C. and then the medium is allowed to return to room temperature over 15 min. The solvents are evaporated under vacuum and the residue is taken up in a diethyl ether/water mixture. The ethereal phase is washed with 0.5N HCl and 10% NaHCO$_3$, and then dried over Na$_2$SO$_4$ and evaporated to give the product.

10.8 g of product are obtained in the form of a yellow gum.

Intermediate 4.3

N-(1H-Indazol-5-yl)-1-(2,4,6-trimethylbenzenesulphonyl)-1H-indazole-3-carboxamide Under argon, a mixture of intermediate 4.2 (431 mg, 1 mmol) and 5-aminoindazole (137 mg, 1 mmol) in THF (10 ml) is heated at 60° C. for 3 days. The THF is evaporated to give the product in the form of a gum.

N-(1H-Indazol-5-yl)-1H-indazole-3-carboxamide

Under argon, an NaOH solution (0.5N, 20 ml, dioxane/H$_2$O 1/1) is added to a suspension of intermediate 4.3 (1 mmol) in dioxane (10 ml). The reaction mixture is heated for 2 h at 60° C. and then concentrated under vacuum and taken up in H$_2$O. The precipitate is filtered and then recrystallized from an isopropanol/petroleum ether mixture.

175 mg of product are obtained in the form of a cream-coloured solid.
m.p.: >250° C.
LC/MS/UV: MH+278 (100%)
$^1$H NMR (500 MHz, DMSO-D6) δ (ppm): 7.28 (t, 1H), 7.44 (t, 1H), 7.50 (d, 1H), 7.65 (d, 1H), 7.75 (d, 1H), 8.04 (s, 1H), 8.23 (d, 1H), 8.43 (s, 1H), 10.31 (s, 1H), 12.99 (s, 1H), 13.7 (s, 1H).

EXAMPLE 5

Compound No. 7

N-(4-Bromophenyl-1H-indazole-3-carboxamide

Under argon, isobutyl chloroformate (357 µl, 2.75 mmol) is added at 0° C. to an indazole-3-carboxylic acid solution (405 mg, 2.5 mmol) in THF (50 ml), followed by N-methylmorpholine (302 μl, 2.75 mmol). The reaction mixture is stirred for 15 min at 0° C. and then 4-bromoaniline (860 mg, 5 mmol) is added. The ice bath is removed and the stirring is maintained overnight. The solvent is evaporated under vacuum. The residue is taken up in an AcOEt/$H_2O$ mixture. The evaporation of the organic solution after drying over $MgSO_4$ gives a crude compound (1.27 g) which is chromatographed on silica, eluting with $CH_2Cl_2$. The compound thus obtained is recrystallized from isopropanol.

572 mg of product are obtained.

m.p.: >250° C.

LC/MS/UV: MH+316

$^1$H NMR (500 MHz, DMSO-D6) δ (ppm): 7.29 (t, 1H), 7.45 (t, 1H), 7.52 (d, 2H), 7.65 (d, 1H), 7.89 (d, 2H), 8.20 (d, 1H), 10.52 (s, 1H), 13.81 (s, 1H).

EXAMPLE 6

Compound No. 12

Ethyl 3-(1H-indazole-3-carbonylamino)benzoate

This compound is synthesized in a manner similar to the procedure described in Example 5. The synthesis is carried out on the scale of 5 mmol. The final compound is recrstallized from AcOEt.

390 mg of product are obtained in the form of a yellow solid.

m.p.: 187-188° C.

LC/MS/UV: MH+310 (100%)

$^1$H NMR (500 MHz, DMSO-D6) δ (ppm): 1.33 (t, 3H), 4.32 (q, 2H), 7.30 (t, 1H), 7.48 (m, 2H), 7.67 (m, 2H), 8.11 (d, 1H), 8.22 (d, 1H), 8.63 (s, 1H), 10.62 (s, 1H), 13.9 (s, 1H).

EXAMPLE 7

Compound No. 13

3-(1H-Indazole-3-carbonylamino)benzoic acid

A suspension of the compound obtained in Example 6 (310 mg, 1 mmol) in dioxane (10 ml) is reacted with aqueous NaOH (0.5N, 10 ml, 5 mmol). The reaction mixture is heated overnight at 50° C. and is then concentrated under vacuum, diluted with $H_2O$ and acidified with 6N HCl. The resulting suspension is filtered. The solid is washed with $H_2O$, isopropanol and diethyl ether and then dried under vacuum.

230 mg of product are obtained.

m.p.: >250° C.

LC/MS/UV: MH+282 (100%)

$^1$H NMR (500 MHz, DMSO-D6) δ (ppm): 7.29 (t, 1H), 7.45 (m, 2H), 7.67 (d, 2H), 8.05 (d, 1H), 8.22 (d, 1H), 8.60 (s, 1H), 10.56 (s, 1H), 12.9 (s, 1H), 13.82 (s, 1H).

EXAMPLE 8

Compound No. 22

N-(3-Thiomethylphenyl)-1H-indazole-3-carboxamide

This compound is prepared in a manner similar to the procedure described in Example 4 on the scale of 1.56 mmol. Intermediate 4.2 is reacted with 3-(thiomethyl)aniline overnight at room temperature and the reaction product is treated with NaOH. The reaction mixture is acidified with 6N HCl and is then evaporated under vacuum. The residue is extracted with AcOEt/1N HCl. The AcOEt solution is successively washed with 10% $NaHCO_3$, $H_2O$ and brine. The final compound is washed with MeOH.

260 mg of product are obtained in the form of a powder.

m.p.: 183° C.

LC/MS/UV: MH+284 (100%)

$^1$H NMR (500 MHz, DMSO-D6) δ (ppm): 2.49 (s, 3H), 6.97 (d, 1H), 7.27 (m, 2H), 7.45 (t, 1H), 7.66 (d, 1H), 7.69 (d, 1H), 7.88 (s, 1H), 8.21 (d, 1H), 10.35 (s, 1H), 13.79 (s, 1H).

EXAMPLE 9

Compound No. 34

N-(Pyridin-4-yl)-5-pyridin-3-yl-1H-indazole-3-carboxamide hydrochloride

Intermediate 9.1

5-Iodo-1H-indazole-3-carboxylic acid

5-Iodoisatin (5 g, 18.3 mmol) is heated in the presence of sodium hydroxide (0.77 g, 19.2 mmol in 12 ml $H_2O$) until dissolution is obtained and then the reaction mixture is cooled to 0° C. A sodium nitrite solution cooled beforehand to 0° C. (1.26 g, 18.3 mmol in 5.5 ml $H_2O$) is added. The paste obtained is added in small portions, with vigorous stirring, to a sulphuric acid solution (3.40 g, 34.8 mmol in 37 ml $H_2O$) precooled to 0° C. so that the temperature does not exceed 4° C. The stirring is maintained for 15 min and then a tin chloride solution ($SnCl_2.2H_2O$, 9.91 g, 43.9 mmol in 15 ml concentrated HCl) is slowly added such that the temperature does not exceed 4° C. The medium is allowed to react for several hours. The reaction mixture is filtered. The solid is washed with boiling water and then taken up in ethanol in the hot state. The insoluble impurities are removed by filtration.

2 g of product are obtained.

Intermediate 9.2

Sodium 5-iodo-1-(2-trimethylsilylethoxymethyl)-1H-indazole-3-carboxylate

Under argon, intermediate 9.1 (20 g, 70 mmol) is added at 0° C. to sodium hydride (6.16 g, 55% in oil, 140 mmol) in anhydrous THF (200 ml). The temperature is allowed to rise to room temperature and stirring is maintained for 20 min. The reaction mixture is again cooled at 0° C. and 2-(trimethylsilyl)ethoxymethyl chloride (12.25 g, 73.5 mmol) in solution in THF (75 ml) is slowly introduced. The reaction is stirred for a few minutes at 0° C. and then for 3 h at room temperature. 80 ml of water are added. The THF is evaporated under vacuum and the insoluble matter is filtered. The solid is washed with $H_2O$ and then with a diethyl ether/petroleum ether mixture and finally with diethyl ether. The solid obtained is dried under vacuum over potassium hydroxide.

20.71 g of product are obtained in the form of a yellow powder.

Intermediate 9.3

N-(Pyridin-4-yl)-5-iodo-1-(2-trimethylsilylethoxymethyl)-1H-indazole-3-carboxamide Under argon, an isopropyl chloroformate solution in toluene (1M, 12 ml) is slowly added, at a temperature of −10° C., to a solution of intermediate 9.2 (5.02 g, 11.4 mmol) in anhydrous THF (50 ml), followed dropwise by N-methylmorpholine (1.22 g, 12 mmol). The temperature is kept for 5 min at −10° C. and then the cooling bath is removed. The mixture is stirred for 25 min at room temperature and then cooled again and a 4-aminopyridine solution (1.13 g, 12 mmol) in THF is added. The reaction mixture is then stirred overnight at room temperature, filtered and concentrated under vacuum. The crude product is chromatographed on silica gel (500 g), eluting according to a gradient from $CH_2Cl_2$ to AcOEt.

4.17 g of product are obtained.

Intermediate 9.4

N-(pyridin-4-yl)-5-pyridinyl-3-yl-1-(2-trimethylsilylethoxymethyl)-1H-indazole-3-carboxamide Under argon, pyridine-3-boronic acid (299 mg, 1.15 equiv.) is added to a solution of intermediate 9.3 (685 mg, 1.38 mmol) in dimethoxyethane (DME) (5.5 ml), followed by an aqueous $Na_2CO_3$ solution (734 mg/2.7 ml $H_2O$, 5 equiv.). The reactor is degassed several times with argon and then, under argon, tetrakis(triphenylphosphine)palladium (48 mg, 0.03 equiv.) is added. The reaction mixture is heated at 85° C. overnight. The solvents are evaporated under vacuum and the residue is extracted with AcOEt/$H_2O$. The organic phase is dried and evaporated. The crude product is chromatographed on silica gel (200 g). Elution with AcOEt/MeOH (95/5) gives, after evaporation, 370 mg of product.

N-(Pyridin-4-yl)-5-pyridin-3-yl-1H-indazole-3-carboxamide hydrochloride

Under argon, a tetrabutylammonium fluoride (TBAF) solution in THF (1M, 6 ml, 5 equiv.), water (0.2 ml) and ethylenediamine (0.20 ml, 3 mmol, 2.5 equiv.) are added to a solution of intermediate 9.4 (530 mg, 1.19 mmol) in THF (15 ml). The reaction mixture is heated at 60° C. for 3 days. Additional tetrabutylammonium fluoride (1N, 3 ml) is added. The heating is maintained for an extra night. The reaction mixture is acidified with 4N HCl (1.2 ml), concentrated under vacuum and then diluted with $H_2O$. The precipitate is filtered, washed with $CH_3OH$ and diethyl ether. The solid obtained is recrystallized from $CH_2Cl_2$/MeOH.

190 mg of product are obtained in the form of a white powder.

m.p.: 196° C.

LC/MS/UV: MH+316 (96.8%)

$^1$H NMR (500 MHz, DMSO-D6) δ (ppm): 7.53 (dd, 1H), 7.84 (s, 2H), 7.99 (d, 2H), 8.13 (d, 1H), 8.46 (s, 1H), 8.50 (d, 1H), 8.59 (d, 1H), 8.92 (s, 1H), 10.86 (s, 1H), 14.1 (s, 1H).

EXAMPLE 10

Compound No. 35

N-(Pyridin-4-yl)-5-(4-methyl-[3,4']bipyridinyl-5-yl)-1H-indazole-3-carboxamide hydrochloride Intermediate 10.1

3,5-Dibromo-4-methylpyridine

Under argon, an n-butyllithium solution in hexane (1.6N, 16 ml) is added dropwise to a diisopropylamine solution (3.6 ml, 1.02 equiv.) in anhydrous THF (145 ml) kept at −10° C. The reaction mixture is cooled to −78° C. and then a 3,5-dibromopyridine solution (5.92 g, 25 mmol) in THF (200 ml) cooled to −78° C. is added dropwise. The reaction mixture is stirred for 30 min and then methyl iodide (2.17 ml, 1.4 equiv.) is added dropwise. The stirring is maintained for 2 h at −78° C. A saturated aqueous $NH_4Cl$ solution (120 ml) is added. After evaporation of the solvents, the reaction mixture is extracted with AcOEt. The organic phase is washed with brine, dried over $MgSO_4$ and evaporated. The yellow solid obtained is taken up in AcOEt. The suspension is filtered. The filtrate is evaporated and then the residue is chromatographed on silica gel, eluting with a petroleum ether/AcOEt (97.5/2.5) mixture.

1.67 g of product are obtained in the form of a white solid.

Intermediate 10.2

5-Bromo-4-methyl-[3,4']bipyridinyl

Under argon, pinacolyl ester of pyridine-4-boronic acid (910 mg, 4.45 mmol), an aqueous $Na_2CO_3$ solution (2.35 g/9 ml $H_2O$) and finally tetrakis(triphenylphosphine)palladium (153 mg) are added to a solution of intermediate 10.1 (1.3 g, 5.18 mmol) in DME (18 ml). The mixture is heated at 85° C. for 2 days. The solvent is evaporated and then the residue is extracted with AcOEt/$H_2O$. The compound obtained after washing the organic solution with brine, drying over $MgSO_4$ and evaporation is chromatographed on silica gel (200 g), eluting with an AcOEt/petroleum ether (1/1) mixture.

440 mg of product are obtained in the form of an oil.

Intermediate 10.3

N-(Pyridin-4-yl)-5-(4,4,5,5-tetramethyl-[1,3,2]dioxaborolan-2-yl)-1-(2-trimethylsilylethoxymethyl)-1H-indazole-3-carboxilic A mixture of intermediate 9.3 (3.77 g, 7.6 mmol), bis(pinacolato)diborane (2.12 g, 8.3 mmol), potassium acetate (2.24 g) in dimethyl sulphoxide (DMSO) (50 ml) is degassed with argon. 1,1'-Bis(diphenylphosphino)ferrocenedichloropalladiumII (310 mg, 0.38 mmol, 0.05 equiv.) is added under argon. The reaction mixture is heated at 80° C. for 1.5 h. Extraction with AcOEt/$H_2O$ makes it possible to isolate an orange-coloured oil which is chromatographed on silica gel, eluting with AcOEt. The yellow oil obtained is crystallized from diethyl ether.

2.56 g of product are obtained in the form of a white powder.

Intermediate 10.4

N-(Pyridin-4-yl)-5-(4-methyl-[3,4']bipyridinyl-5-yl)-1-(2-trimethylsilylethoxymethyl)-1H-indazole-3-carboxamide An aqueous $Na_2CO_3$ solution (686 mg/2.6 ml) is added to a solution of intermediate 10.3 (640 mg, 1.29 mmol) and of intermediate 10.2 (370 mg, 1.15 equiv.) in DME (6 ml). The reaction mixture is degassed with argon. Tetrakis(triphenylphosphine)palladium (46 mg) is added under argon. The reaction mixture is heated at 85° C. overnight. The solvent is evaporated. Extraction with AcOEt/$H_2O$ makes it possible to isolate an oil which is crystallized from an AcOEt/petroleum ether mixture.

530 mg of product are obtained in the form of a white powder.

N-(Pyridin-4-yl)-5-(4-methyl-[3,4']bipyridinyl-5-yl)-1H-indazole-3-carboxamide hydrochloride The protecting group SEM of intermediate 10.4 is cleaved in the presence of tetrabutylammonium fluoride in a manner similar to the procedure described in Example 9. The crude product is taken up in MeOH/Et$_2$O. The compound obtained is isolated by filtration and washed with MeOH.

265 mg of product are obtained in the form of a powder.
m.p.: 192° C.
LC/MS/UV: MH+407 (96.1%)
$^1$H NMR (500 MHz, DMSO-D6) δ (ppm): 2.13 (s, 3H), 7.65 (m, 3H), 7.90 (d, J=8.5, 1H), 8.01 (d, J=7.2, 2H), 8.32 (s, 1H), 8.54 (s, 1H), 8.55 (d, J=6.2, 2H), 8.60 (s, 1H), 8.79 (d, J=5.7, 2H), 10.90 (s, 1H), 13 (s, 1H).

EXAMPLE 11

Compound No. 36

N-(Pyridin-4-yl)-5-(5-carbamoyl-4-methylpyridin-3-yl)-1H-indazole-3-carboxamide

Intermediate 11.1

5-Bromo-N-tert-butyl-4-methylnicotinamide

Under argon, an n-butyllithium solution in hexane (1.55N, 6.6 ml) is added dropwise to a solution of 3,5-dibromo-4-methylpyridine (intermediate 10.1, 2.51 g, 10 mmol) kept at −100° C. After stirring for 10 min, tert-butyl isocyanate (2.28 ml, 20 mmol) is added. The stirring is maintained for 20 min at −100° C. and then for 1 h at −78° C. and at room temperature overnight. An aqueous NH$_4$Cl solution is added to the reaction mixture. Extraction with AcOEt/H$_2$O gives a brown solid which is taken up in an AcOEt/petroleum ether mixture. The compound obtained is isolated by filtration.

1.6 g of product are obtained.

Intermediate 11.2

5-Bromo-4-methylnicotinamide

Intermediate 11.1 (1.4 g, 5.18 mmol) is reacted with 90% H$_2$SO$_4$ (25 ml). The mixture is stirred at room temperature for 3 days. The reaction mixture is neutralized with a saturated aqueous Na$_2$CO$_3$ solution, and is then extracted with AcOEt. The solid obtained is taken up in AcOEt and filtered.

880 mg of product are obtained in the form of a powder.

Intermediate 11.3

N-(Pyridin-4-yl)-5-(5-carbamoyl-4-methylpyridin-3-yl)-1-(2-trimethylsilanylethoxymethyl)-1H-indazole-3-carboxamide This compound is synthesized in a manner similar to intermediate 10.4, by a Suzuki reaction between intermediate 10.3 and intermediate 11.2, on the scale of 1.29 mmol. It is recrystallized from a CHCl$_3$/AcOEt mixture.

530 mg of product are obtained in the form of a white solid.

N-(Pyridin-4-yl)-5-(5-carbamoyl-4-methylpyridin-3-yl)-1H-indazole-3-carboxamide

Intermediate 11.3 (550 mg, 1.09 mmol) is reacted with trifluoroacetic acid (TFA) for 5 min at 0° C. and then for 1.5 h at room temperature. The TFA is evaporated under vacuum. The traces of TFA are removed by coevaporation with toluene. The white solid obtained is reacted with an ethylenediamine solution (366 μl, 5.4 mmol) in THF (10 ml). The reaction mixture is heated under reflux overnight. The reaction mixture is filtered and then washed with an MeOH/H$_2$O mixture.

270 mg of product are obtained in the form of a white solid.
m.p.: >250° C.
LC/MS/UV: MH+373 (100%)
$^1$H NMR (500 MHz, DMSO-D6) δ (ppm): 2.25 (s, 3H), 7.54 (dd, J=8.7, J=1.1, 1H), 7.73 (s, 1H), 7.87 (d, J=8.6, 1H), 7.98 (d, J=6.3, 2H), 8.09 (s, 1H), 8.21 (s, 1H), 8.49 (d, J=5.0, 2H), 8.54 (s, 1H), 8.59 (s, 1H), 10.87 (s, 1H), 14.1 (s, 1H).

EXAMPLE 12

Compound No. 37

N-(Pyridin-4-yl)-5-(4-methyl-5-phenoxymethylpyridin-3-yl)-1H-indazole-3-carboxamide hydrochloride Intermediate 12.1

5-Bromo-4-methylpyridine-3-carbaldehyde

Under argon, an n-butyllithium solution in hexane (1.55N, 4.6 ml) is added dropwise to a 3,5-dibromo-4-methylpyridine solution (intermediate 10.1, 1.76 g, 7 mmol) kept at −100° C. After stirring for 5 min, DMF (0.84 ml, 1.54 equiv.) is added dropwise. The stirring is maintained for 20 min at −100° C. and then for 1 h at −78° C. An aqueous NH$_4$Cl solution is added and the reaction mixture is extracted with a diethyl ether/water mixture. The yellow solid obtained is purified on silica gel (100 g), eluting with AcOEt/petroleum ether (1/4).

610 mg of product are obtained in the form of a colourless oil.

Intermediate 12.2

(5-Bromo-4-phenylpyridin-3-yl)methanol

Sodium borohydride (358 mg, 9.46 mmol) is added at 0° C. to intermediate 12.1 (610 mg, 3.05 mmol) in solution in MeOH (15 ml). The reaction mixture is stirred for 1.5 h and is then diluted with AcOEt/H$_2$O. Extraction with AcOEt gives a white solid which is chromatographed on silica gel (100 g). Elution with AcOEt gives 420 mg of product.

Intermediate 12.3

3-Bromo-4-methyl-5-phenoxymethylpyridine

Phenol (0.22 ml, 2.50 mmol), triphenylphosphine (655 mg, 2.50 mmol) and diethylazodicarboxylate (0.393 ml, 2.50 mmol) are added to intermediate 12.2 (420 mg, 2.08 mmol) in solution in a mixture of THF (10 ml) and toluene (3 ml). The reaction mixture is stirred for 3 days at room temperature and is then extracted with AcOEt/H$_2$O. The crude compound is purified on silica gel (100 g). Elution with AcOEt/petroleum ether (1/1) gives a compound which is taken up in AcOEt and washed with 1N NaOH.

380 mg of product are obtained in the form of a colourless oil.

Intermediate 12.4

N-(Pyridin-4-yl)-5-(4-methyl-5-phenoxymethylpyridin-3-yl)-1-(2-trimethylsilylethoxymethyl)-1H-indazole-3-carboxamide This compound is synthesized in a manner similar to intermediate 10.4, by a Suzuki reaction between intermediates 10.3 and 12.3, on a scale of 1.37 mmol. It is chromatographed on silica gel, eluting with AcOEt.

567 mg of product are obtained in the form of a colourless oil.

N-(Pyridin-4-yl)-5-(4-methyl-5-phenoxymethylpyridin-3-yl)-1H-indazole-3-carboxamide hydrochloride The protecting group SEM of intermediate 12.4 is cleaved with tetrabutylammonium fluoride in a manner similar to the procedure described in Example 9, on the scale of 1 mmol. The compound is taken up in MeOH and then filtered.

230 mg of product are obtained in the form of a white powder.

m.p.: 160° C.
LC/MS/UV: MH+436 (98.8%)
$^1$H NMR (500 MHz, DMSO-D6) δ (ppm): 2.40 (s, 3H), 5.32 (s, 2H), 7.07 (t, J=4.85, 1H), 7.19 (d, J=7.9, 2H), 7.42 (t, J=5.3, 2H), 7.56 (dd, J=8.4, J=1.5, 1H), 7.88 (d, J=8.6, 1H), 7.99 (d, J=6.3, 2H), 8.23 (s, 1H), 8.53 (s, 1H), 8.54 (d, J=6.0, 2H), 8.70 (s, 1H), 10.88 (s, 1H), 14.05 (s, 1H)

EXAMPLE 13

Compound No. 41

N-(Pyridin-4-yl)-5-isoquinolin-4-yl-1H-indazole-3-carboxamide

Intermediate 13.1

5-Iodo-1H-indazole-3-carbaldehyde

Under argon, 1 g of sodium nitrite (27.6 g, 400 mmol) is added in portions to a suspension of 5-iodoindole (9.722 g, 40 mmol) in water, followed dropwise by a 6N HCl solution (59 ml). The temperature of the reaction mixture is kept under 15° C. and then the reaction mixture is left under vigorous stirring at room temperature overnight. The nitrous vapours are expelled under an argon stream and then the reaction mixture is filtered. Washing the solid with H$_2$O followed by purification on silica gel (600 g), eluting according to an elution gradient from CH$_2$Cl$_2$ to a CH$_2$Cl$_2$/AcOEt (9/1) mixture, makes it possible to isolate 1.37 g of product in the form of a brown solid.

LC/MS/UV: MH+273 (88.6%)

Intermediate 13.2

5-Iodo-1-(2-trimethylsilylethoxymethyl)-1H-indazole-3-carbaldehyde

Under argon, intermediate 13.1 (2.58 g, 9.5 mmol) is added to a suspension of sodium hydride (50% in oil, 0.50 g, 10.4 mmol) in anhydrous DMF (10 ml), followed dropwise by a trimethylsilylethoxymethyl chloride solution (SEMCI, 1.60 g, 9.6 mmol) in DMF (5 ml). The stirring is maintained for 1 h at room temperature. Water is added and then the DMF is evaporated under vacuum. The residue is taken up in CH$_2$Cl$_2$. The organic solution is washed with brine, dried and then evaporated under vacuum. The crude product is chromatographed on silica gel (500 g). Elution with CH$_2$Cl$_2$ gives the product in the form of a brown viscous oil.

Intermediate 13.3

5-Isoquinolin-4-yl-1-(2-trimethylsilylethoxymethyl)-1H-indazole-3-carbaldehyde

Under argon, isoquinolin-4-ylboronic acid hydrochloride (0.56 g, 2.66 mmol), an aqueous Na$_2$CO$_3$ solution (1.42 g, 13.4 mmol in 5 ml H$_2$O) and tetrakis(triphenylphosphine)palladium0 (0.160 g, 0.14 mmol, 0.05 equiv.) are added to a solution of intermediate 13.2 (1.07 g, 2.66 mmol) in DME (10 ml). The reaction mixture is heated by means of an oil bath regulated at 85° C. for 5 h and is then concentrated under vacuum. The residue is taken up in AcOEt. The organic solution is washed with brine, dried and then evaporated to give a crude product which is purified on silica gel (150 g). The elution according to a gradient ranging from CH$_2$Cl$_2$ to CH$_2$Cl$_2$/AcOEt (9/1) gives 0.84 g of product.

Intermediate 13.4

5-Isoquinolin-4-yl-1-(2-trimethylsilylethoxymethyl)-1H-indazole-3-carboxylic acid 2-Methyl-2-butene (5 ml) and DMF (5 ml) are added to a solution of intermediate 13.3 (0.50 g, 1.24 mmol) in DMF (5 ml) maintained at a temperature between 0° C. and −5° C., cooled by a bath consisting of a mixture of ice and salt, followed by an aqueous solution (10 ml) of sodium chlorite (1.12 g) and sodium dihydrogen phosphate (1.37 g, in hydrate form). The temperature of the reaction mixture is kept at 0° C. for 30 min, and then the reaction mixture is stirred for 4.5 h at room temperature and, after acidification with 6N HCl (5 ml), overnight. The reaction mixture is evaporated. The residue is taken up in AcOEt. This solution is washed with H$_2$O and brine, dried over Na$_2$SO$_4$ and evaporated to give 0.50 g of product in the form of a white solid.

Intermediate 13.5

N-(Pyridin-4-yl)-5-isoquinolin-4-yl-1-(2-trimethylsilylethoxymethyl)-1H-indazole-3-carboxamide Under argon, isopropyl chloroformate (1M in toluene, 1.2 ml) and N-methylmorpholine (0.120 g, 1.2 mmol) are added to a solution of intermediate 13.4 (0.50 g, 1.19 mmol) in anhydrous THF (10 ml) kept at a temperature between −5° C. and 0° C. The medium is allowed to react for 15 min before adding 4-aminopyridine (0.114 g, 1.2 mmol). The reaction mixture is stirred for 30 min at 0° C. and then overnight at room temperature. It is then evaporated and taken up in AcOEt. The organic solution is washed with brine, dried over Na$_2$SO$_4$ and evaporated. The oil obtained is purified on silica gel. Elution with a CH$_2$Cl$_2$/MeOH (9/1) mixture makes it possible to isolate 250 mg of product in the form of a yellow oil.

N-(Pyridin-4-yl)-5-isoquinolin-4-yl-1H-indazole-3-carboxamide

Under argon, a mixture of intermediate 13.5 (0.250 g, 0.5 mmol), 1,2-diaminoethane (0.150 g, 2.5 mmol) and tetrabutylammonium fluoride in THF (1M, 5 ml) is heated at 70° C.

overnight. The reaction mixture is evaporated under vacuum. The residue is taken up in AcOEt. This solution is washed with a saturated aqueous $NaHCO_3$ solution and brine, and then dried and evaporated. The solid obtained is washed with diethyl ether and then purified on silica gel (50 g). The compound obtained is eluted with an AcOEt/MeOH (9/1) mixture. It is taken up in a diethyl ether/petroleum ether mixture and then filtered.

182 mg of product are obtained in the form of a white solid.
m.p.: >250° C.
LC/MS/UV: MH+366 (99.4%)
$^1$H NMR (500 MHz, DMSO-D6) δ (ppm): 7.65 (d, J=8.5, 1H), 7.76 (t, J=7.3, 1H), 7.81 (t, J=7.4, 1H), 7.88 (dd, J=8.4, J=3.3, 2H), 7.92 (d, J=6.1, 2H), 8.26 (d, J=8.0, 1H), 8.34, (s, 1H), 8.46 (d, J=5.9, 2H), 8.52 (s, 1H), 9.38 (s, 1H), 10.85 (s, 1H), 14.2 (s, 1H).

EXAMPLE 14

Compound No. 45

4-[5-(Isoquinolin-4-yl)-1H-indazole-3-carbonylamino]benzoic acid

Intermediate 14.1

Ethyl 4-[5-(isoquinolin-4-yl)-1-(2-trimethylsilylethoxymethyl)-1H-indazole-3-carbonylamino] benzoate This compound is prepared in a manner similar to intermediate 13.5 by coupling intermediate 13.4 with ethyl 4-aminobenzoate, on the scale of 2.4 mmol. The crude compound is purified on silica gel (80 g). An elution gradient from $CH_2Cl_2$ to $CH_2Cl_2$/AcOEt (7/3) makes it possible to isolate 0.62 g of product in the form of an oil.

Intermediate 14.2

Ethyl 4-[5-(isoquinolin-4-yl)-1H-indazole-3-carbonylamino]benzoate

The protecting group SEM of intermediate 14.1 is cut with TBAF in a manner similar to the procedure described in Example 13, on the scale of 1.1 mmol. This compound is taken up in diethyl ether and then filtered.

292 mg of a mixture of the expected ester and of the corresponding acid are obtained.

4-[5-(Isoquinolin-4-yl)-1H-indazole-3-carbonylamino]benzoic acid

An aqueous lithium hydroxide solution (36 mg/1 ml $H_2O$, 1.48 mmol) is added to a suspension of intermediate 14.2 (290 mg, 0.67 mmol) in THF (5 ml). The reaction mixture is heated under reflux overnight and then acidified with 1N HCl (1.5 ml). Evaporation of the solvents gives a solid which is taken up in water, filtered, washed with water and diethyl ether ($Et_2O$). The solid obtained is dried under vacuum in the presence of $P_2O_5$.

0.278 g of product is obtained in the form of a grey solid.
m.p.: >260° C.
LC/MS/UV: MH+409 (100%)
$^1$H NMR (500 MHz, DMSO-D6) δ (ppm): 7.5-8.6 (m, 12H), 9.42 (s, 1H), 10.75 (s, 1H), 12.67 (s, 1H), 14.08 (s, 1H).

EXAMPLE 15

Compound No. 46

N-(Pyridin-4-yl)-5-amino-1H-indazole-3-carboxamide

Intermediate 15.1

5-Nitro-1H-indazole-3-carbaldehyde

This intermediate is prepared in a manner similar to intermediate 13.1 by reacting nitrous acid with 5-nitroindole on the scale of 30 mmol. The reaction mixture is extracted with AcOEt. The organic phase is washed with brine and then dried over $Na_2SO_4$. Evaporation under vacuum gives a reddish solid which is washed with petroleum ether and dried under vacuum.

5.51 g of product are obtained.

Intermediate 15.2

5-Nitro-1-(2,4,6-trimethylbenzenesulphonyl)-1H-indazole-3-carbaldehyde

Under argon, 4-dimethylaminopyridine (3.63 g, 29.71 mmol) is added to a solution of intermediate 15.1 (5.4 g, 28.25 mmol) in anhydrous $CH_2Cl_2$ (250 ml) kept at 0° C. by an ice bath, followed after a few minutes, dropwise by 2-mesitylenesulphonyl chloride (6.50 g, 29.71 mmol) in solution in $CH_2Cl_2$ (100 ml). The reaction mixture is stirred for 1 h at 0° C. and then overnight at room temperature. Water is added. The reaction mixture is extracted with $CH_2Cl_2$. The organic phase is washed with brine, dried over $Na_2SO_4$ and evaporated to give a brown solid which is purified by chromatography on silica gel (300 g), eluting with $CH_2Cl_2$. A solid separates after concentrating the fractions under vacuum. It is filtered and then washed with diethyl ether and petroleum ether.

5 g of product are obtained in the form of a beige solid.

Intermediate 15.3

5-Nitro-1-(2,4,6-trimethylbenzenesulphonyl)-1H-indazole-3-carboxylic acid

The aldehyde functional group of intermediate 15.2 is oxidized to carboxylic acid with sodium chlorite in a manner similar to intermediate 13.4, on the scale of 13.4 mmol.

The crude product, a yellow oil, is crystallized from a petroleum ether/diethyl ether mixture.

4.47 g of product are obtained in the form of a white solid.

Intermediate 15.4

N-(Pyridin-4-yl)-5-nitro-1-(2,4,6-trimethylbenzenesulphonyl)-1H-indazole-3-carboxamide Intermediate 15.4 is obtained in a manner similar to intermediate 13.5 by coupling intermediate 15.3 with 4-aminopyridine, on the scale of 4.78 mmol. The crude reaction product is taken up in diethyl ether. A precipitate forms which is filtered and then purified by chromatography on silica gel (80 g), eluting with an AcOEt/$CH_2Cl_2$ (1/1) mixture.

0.69 g of product is obtained in the form of a white solid.

Intermediate 15.5

N-(Pyridin-4-yl)-5-amino-1-(2,4,6-trimethylbenzenesulphonyl)-1H-indazole-3-carboxamide Intermediate 15.4 (0.35 g, 0.75 mmol) is suspended in ethanol (40 ml). Tin chloride ($SnCl_2$, $2H_2O$, 0.847 g, 3.75 mmol) is added and then the reaction mixture is heated under reflux for 4 h. It is evaporated under vacuum. The residue is taken up in $H_2O$ and the pH is adjusted to pH 8 by adding 2N sodium hydroxide. Extraction with a $CH_2Cl_2/CHCl_3$ mixture followed by washing with brine, drying over $Na_2SO_4$ and then evaporation under vacuum gives a crude product which is taken up in a diethyl ether/petroleum ether mixture and then filtered.

0.282 g of product is obtained in the form of a white solid.

N-(Pyridin-4-yl)-5-amino-1H-indazole-3-carboxamide

A 1N sodium hydroxide solution (3.18 ml) is added to intermediate 15.5 (0.277 g, 0.636 mmol) in solution in 1,4-dioxane. The reaction mixture is heated at 70° C. with an oil bath for 4 h. The reaction mixture is neutralized by adding 1N HCl solution (3.2 ml) and then evaporated. The residue is taken up in water. The pH is adjusted to neutral pH. A precipitate forms which is filtered, washed with water and then with diethyl ether.

121 mg of product are obtained in the form of a brown solid.

m.p.: >260° C.
LC/MS/UV: MH+254 (100%)
$^1$H NMR (500 MHz, DMSO-D6) δ (ppm): 5.13 (s, 2H), 6.88 (d, 1H), 7.30 (s, 1H), 7.38 (d, 1H), 7.78 (d, 2H), 8.44 (d, 2H), 10.49 (s, 1H), 13.46 (s, 1H).

EXAMPLE 16

Compound No. 47

N-(Pyridin-4-yl)-5-(3-methylbutyrylamino)-1H-indazole-3-carboxamide

Intermediate 16.1

N-(Pyridin-4-yl)-5-(3-methylbutyrylamino)-1-(2,4,6-trimethylbenzenesulphonyl)-1H-indazole-3-carboxamide Under argon, N,N-diisopropylethylamine (72 mg, 0.55 mmol) is added to a solution of intermediate 15.5 (240 mg, 0.55 mmol) in anhydrous $CH_2Cl_2$ (5 ml) kept at 0° C., followed by isovaleryl chloride (68 mg, 0.55 mmol) in solution in $CH_2Cl_2$ (2 ml). Stirring is maintained for 30 min at 0° C. and then overnight at room temperature. The reaction mixture is evaporated. The residue is taken up in AcOEt. The organic solution is washed with $NaHCO_3$, brine and then dried over $Na_2SO_4$. The evaporation residue is taken up in diethyl ether. The compound obtained is isolated by filtration and then washed with diethyl ether.

198 mg of product are obtained.

N-(Pyridin-4-yl)-5-(3-methylbutyrylamino)-1H-indazole-3-carboxamide

This compound is prepared by cleaving the protecting group mesitylenesulphonyl of intermediate 16.1 with sodium hydroxide in a manner similar to the procedure described in Example 15.

76.5 mg of product are obtained in the form of a brown solid.

m.p.: >260° C.
LC/MS/UV: MH+338 (95.3%)
$^1$H NMR (500 MHz, DMSO-D6) δ (ppm): 0.95 (d, 6H), 2.12 (m, 1H), 2.21 (d, 2H), 7.63 (s, 2H), 8.15 (d, 2H), 8.59 (d, 2H), 8.61 (s, 1H), 10.02 (s, 1H), 11.13 (s, 1H), 13.96 (s, 1H).

EXAMPLE 17

Compound No. 49

N-(Pyridin-4-yl)-5-nitro-1H-indazole-3-carboxamide

The protecting group mesitylenesulphonyl of the intermediate 15.4 is cleaved with sodium hydroxide, in a manner similar to Example 15, on the scale of 0.7 mmol.

0.20 g of product is obtained in the form of a yellow solid.
m.p.: >260° C.
LC/MS/UV: MH+284 (100%)
$^1$H NMR (500 MHz, DMSO-D6) δ (ppm): 7.93 (d, J=9.0, 1H), 8.13 (d, J=6.3, 2H), 8.32 (dd, J=8.8, J=1.9, 1H), 8.61 (d, J=6.9, 2H), 9.08 (d, J=1.9, 1H), 11.35 (s, 1H), 14.65 (s, 1H).

EXAMPLE 18

Compound No. 50

N-(Pyridin-4-yl)-5-iodo-1H-indazole-3-carboxamide

The protecting group SEM of the intermediate 9.3 is cleaved with TBAF, in a manner similar to the procedure described in Example 13, on the scale of 0.5 mmol. The crude reaction product is washed with diethyl ether.

297 mg of product are obtained.
m.p.: >260° C.
LC/MS/UV: MH+365 (100%)
$^1$H NMR (500 MHz, DMSO-D6) δ (ppm): 7.59 (d, 1H), 7.76 (d, 1H), 8.09 (d, 2H), 8.54 (d, 2H), 8.61 (s, 1H), 11.01 (s, 1H), 14.16 (s, 1H).

EXAMPLE 19

Compound No. 51

N-(Pyridin-4-yl)-5-cyano-1H-indazole-3-carboxamide

Intermediate 19.1

3-Formyl-1H-indazole-5-carbonitrile

5-Cyanoindole (2.85 g, 20 mmol) is added to an aqueous sodium nitrite solution (13.80 g, 200 mmol in 400 ml $H_2O$), followed dropwise over 30 min by a 6N HCl solution (30 ml). The reaction mixture is stirred for 3 h and then filtered. The solid is taken up in AcOEt. The organic solution is dried over $Na_2SO_4$ and then evaporated.

The product is obtained in the form of an orange-coloured solid.

Intermediate 19.2

3-Formyl-1-(2,4,6-trimethylbenzenesulphonyl)-1H-indazole-5-carbonitrile

4-Dimethylaminopyridine (2.21 g, 21 mmol) and a mesitylenesulphonyl chloride solution (4.60 g, 21 mmol) in anhydrous THF (50 ml) are added to a solution of intermediate 19.1 (20 mmol) in anhydrous THF (200 ml) kept at 0° C. The reaction mixture is stirred at room temperature overnight. It is filtered and then evaporated. The residue is taken up in AcOEt. The organic solution is washed with 1N HCl, H$_2$O and 10% NaHCO$_3$ and then dried and concentrated under vacuum. The residue is precipitated by adding petroleum ether.

6.11 g of product are obtained in the form of an orange-coloured solid.

Intermediate 19.3

5-Cyano-1-(2,4,6-trimethylbenzenesulphonyl)-1H-indazole-3-carboxylic acid

A solution of intermediate 19.2 (6.0 g, 17 mmol) in DMF (100 ml) is cooled to 0° C. 2-Methyl-2-butene (70 ml) and then an aqueous solution (125 ml) of sodium chlorite (80%, 15.3 g, 136 mmol) and sodium dihydrogen phosphate (NaH$_2$PO$_4$.H$_2$O, 18.7 g, 136 mmol) are added. The reaction mixture is stirred for 1 h at room temperature. A 4N HCl solution (100 ml) is added dropwise and the reaction mixture is stirred for 2 h. The mixture is diluted with water and extracted with AcOEt. The organic phase is washed with water, dried and evaporated. The residue is precipitated from a diethyl ether/petroleum ether mixture.

5.32 g of product are obtained in the form of a cream-coloured powder.

Intermediate 19.4

Isopropyl [5-cyano-1-(2,4,6-trimethylbenzene-sulphonyl)-1H-indazol-3-yl]carbonylcarbonate Under argon, an isopropyl chloroformate solution in toluene (1M, 15.8 ml) is added to a solution of intermediate 19.3 (5.32 g, 14.4 mmol) in anhydrous THF (150 ml) kept at 0° C., and N-methylmorpholine (1.74 ml, 15.8 mmol) is added dropwise. The reaction mixture is stirred for 15 min at 0° C. and then for 30 min at room temperature. The solvent is evaporated and the residue is taken up in a diethyl ether/water mixture. The organic phase is washed with water, 0.5N HCl and 5% NaHCO$_3$ and then dried and evaporated.

5.61 g of product are obtained in the form of a cream-coloured solid.

N-(Pyridin-4-yl)-5-cyano-1H-indazole-3-carboxamide

Under argon, 4-aminopyridine (2.32 g, 24.6 mmol) is added to 5.61 g (12.3 mmol) of intermediate 19.4 in solution in anhydrous THF (100 ml). The reaction mixture is heated at 60° C. for 36 h, and then filtered. The solid thus isolated is washed with THF. It is taken up in a CH$_2$Cl$_2$/MeOH mixture and filtered.

3.95 g of product are obtained in the form of a cream-coloured solid.

m.p.: >250° C.
LC/MS/UV: MH+254 (100%)
$^1$H NMR (500 MHz, DMSO-D6) δ (ppm): 7.80 (d, 1H), 7.87 (d, 1H), 7.91 (d, 2H), 8.47 (d, 2H), 8.65 (s, 1H), 10.95 (s, 1H), 14.3 (s, 1H).

EXAMPLE 20

Compound No. 52

Methanesulphonic acid salt of N-(pyridin-4-yl)-5-aminomethyl-1H-indazole-3-carboxamide A solution of the compound obtained in Example 19 (263 mg, 1 mmol) in an AcOH/H$_2$O (25 ml/5 ml) mixture is hydrogenated at atmospheric pressure in the presence of 10% Pd/C (50 mg) for 3 h. The catalyst is filtered and the mixture is concentrated under vacuum. The residue is crystallized from an isopropanol/H$_2$O mixture.

128 mg of product are obtained.
m.p.: >250° C.
LC/MS/UV: MH+268 (100%)
$^1$H NMR (500 MHz, DMSO-D6) δ (ppm): (in agreement with C14H13N5O; 1.5 CH4O3S) 2.31 (d, 2H), 7.60 (d, J=8.8, 1H), 7.82 (d, J=8.7, 1H), 8.21 (s, 3H), 8.38 (s, 1H), 8.43 (d, J=6.8, 2H), 8.77 (d, J=7.0, 2H), 11.79 (s, 1H), 14.32 (s, 1H).

EXAMPLE 21

Compound No. 53

N-(Pyridin-4-yl)-5-bromo-1H-indazole-3-carboxamide

Intermediate 21.1

5-Bromoindazole-3-carbaldehyde

5-Bromoindole (3.93 g, 20 mmol) is added to an aqueous sodium nitrite solution (13.80 g, 200 mmol in 400 ml H$_2$O), followed slowly, over 25 min, by a 6N aqueous HCl solution (30 ml). The reaction mixture is vigorously stirred for 3 h and then filtered. The solid collected is taken up in AcOEt. This solution is dried and evaporated.

Intermediate 21.2

5-Bromo-1-(2,4,6-trimethylbenzenesulphonyl)-1H-indazole-3-carbaldehyde

4-Dimethylaminopyridine (2.21 g, 21 mmol) and a solution of mesitylenesulphonyl chloride (4.60 g, 21 mmol) in anhydrous THF (50 ml) are added to a solution of intermediate 21.1 (20 mmol) in anhydrous THF (200 ml) kept at 0° C. The reaction mixture is stirred at room temperature overnight, and is then filtered and evaporated. The residue is taken up in AcOEt. The organic solution is washed with 1N HCl, H$_2$O and 10% NaHCO$_3$ and then dried and concentrated under vacuum. The residue is purified on silica gel, eluting according to a gradient from AcOEt/petroleum ether (1/9) to AcOEt/petroleum ether (1/4). The purified compound is recrystallized in AcOEt/petroleum ether.

3.60 g of product are obtained in the form of a brown solid.

Intermediate 21.3

5-Bromo-1-(2,4,6-trimethylbenzenesulphonyl)-1H-indazole-3-carboxylic acid

An aqueous solution (40 ml) of sodium chlorite (80%, 4.50 g, 50 mmol) and sodium dihydrogen phosphate (NaH$_2$PO$_4$.H$_2$O, 5.50 g, 40 mmol) is added over 20 min to a solution of intermediate 21.2 (2.04 g, 5 mmol) in DMF (50 ml) and 2-methyl-2-butene (20 ml) cooled to 0° C. The reaction mixture is stirred for 1 h at room temperature. A 4N HCl solution (30 ml) is added dropwise and the reaction mixture is stirred for 2 h. It is diluted with water (100 ml) and extracted with diethyl ether. The organic phase is washed with water, dried and evaporated. The residue is precipitated from a CH$_2$Cl$_2$/petroleum ether mixture.

2.1 g of product are obtained in the form of a brown solid.

Intermediate 21.4

Isopropyl [5-bromo-1-(2,4,6-trimethylbenzene-sulphonyl)-1H-indazol-3-yl]carbonylcarbonate Under argon, a solution of isopropyl chloroformate in toluene (1M, 5.5 ml) is added to a solution of intermediate 21.3 (5 mmol) in anhydrous THF (50 ml) kept at 0° C., followed dropwise by N-methylmorpholine (605 µl, 5.5 mmol). The reaction mixture is stirred for 15 min at 0° C. and then for 30 min at room temperature. The solvent is evaporated and the residue is taken up in a diethyl ether/water mixture. The organic phase is washed with water, 0.5N HCl and 5% NaHCO$_3$ and then dried and evaporated.

2.58 g of product are obtained in the form of a black-red gum.

N-(Pyridin-4-yl)-5-bromo-1H-indazole-3-carboxamide

Under argon, 4-aminopyridine (941 mg, 10 mmol) and intermediate 21.4 (5 mmol) in solution in anhydrous THF (35 ml) are heated at 60° C. for 36 h. The reaction mixture is evaporated. The residue is taken up in diethyl ether. The ethereal solution is evaporated. The residue is recrystallized from MeOH/CH$_2$Cl$_2$.

186 mg of product are obtained.
LC/MS/UV: MH+317 (99.5%)
$^1$H NMR (500 MHz, DMSO-D6) δ (ppm): 7.59 (d, 1H), 7.68 (d, 1H), 7.90 (d, 2H), 8.35 (s, 1H), 8.46 (d, 2H), 10.80 (s, 1H), 14.1 (s, 1H).

EXAMPLE 22

Compound No. 54

N-(Pyridin-4-yl)-5-[4-methyl-5-(pyridin-3-ylcarbamoyl)pyridin-3-yl]-1H-indazole-3-carboxamide Intermediate 22.1

5-Bromo-4-methylnicotinic acid

Under argon, a solution of 3,5-dibromo-4-methylpyridine (intermediate 10.1, 2.51 g, 10 mmol) in anhydrous THF (100 ml) is reacted at a temperature of −100° C. with a solution of n-butyllithium in hexane (1.6N, 6.5 ml). The reaction mixture is stirred for 15 min and then dry ice is added. The temperature is kept for 15 min at −85° C., for 1 h 30 min at −78° C. and for 2 h at room temperature. Water is added. The solvents are evaporated under vacuum and the residue is purified, eluting on diol grafted silica with MeOH.

1.66 g of product are obtained in the form of a white solid.

Intermediate 22.2

5-Bromo-4-methyl-N-pyridin-3-ylnicotinamide

Under argon, O-(7-azabenzotriazol-1-yl)-N,N,N',N'-tetramethyluronium hexafluorophosphate (HATU, 2.36 g, 6.21 mmol) is added to a solution of intermediate 22.1 (1.22 g, 5.65 mmol) in anhydrous DMF (60 ml). The reaction mixture is stirred for 10 min before adding 3-aminopyridine (740 mg, 7.86 mmol). The stirring is maintained for 3 days at room temperature. The DMF is evaporated. The residue is taken up in AcOEt/H$_2$O. The organic phase is washed with 1N HCl. The aqueous phases are combined and brought to a basic pH by adding 1N sodium hydroxide and then extracted with AcOEt. The organic phase is dried over MgSO$_4$ and then evaporated.

1.08 g of product are obtained in the form of a white solid.

Intermediate 22.3

N-(Pyridin-4-yl)-5-[4-methyl-5-(pyridin-3-ylcarbamoyl)pyridin-3-yl]-1-(2-trimethylsilylethoxymethyl)-1H-indazole-3-carboxamide An aqueous Na$_2$CO$_3$ solution (686 mg/2.6 ml) is added to a solution of intermediate 10.3 (640 mg, 1.29 mmol) and of intermediate 22.2 (435 mg, 1.49 mmol) in DME (6 ml). The reaction mixture is degassed with argon. Tetrakis(triphenylphosphine)palladium (46 mg) is added under argon. The reaction mixture is heated at 85° C. overnight. The solvent is evaporated. Extraction with AcOEt/H$_2$O makes it possible to isolate an oil which is crystallized from an AcOEt/CHCl$_3$ mixture.

504 mg of product are obtained in the form of a powder.

N-(Pyridin-4-yl)-5-[4-methyl-5-(pyridin-3-ylcarbamoyl)pyridin-3-yl]-1H-indazole-3-carboxamide The compound is obtained in a manner similar to the procedure described in Example 11 by cleaving the protecting group SEM of intermediate 22.3 (500 mg, 0.86 mmol). The crude product is taken up in MeOH. The compound obtained is isolated by filtration.

340 mg of product are obtained in the form of a white powder.
m.p.: >250° C.
LC/MS/UV: MH+450 (97.7%)
$^1$H NMR (500 MHz, DMSO-D6) δ (ppm): 2.29 (s, 3H), 7.48 (dd, J=8.0, J=4.7, 1H), 7.57 (d, J=8.5), 7.89 (d, J=8.6, 1H), 7.98 (d, J=5.2, 2H), 8.26 (m, 2H), 8.40 (d, J=4.5, 1H), 8.52 (d, J=5.2, 2H), 8.64 (s, 1H), 8.77 (s, 1H), 9.86 (s, 1H), 10.88 (s, 1H), 13.8 (s, 1H).

EXAMPLE 23

Compound No. 55

N-(Pyridin-4-yl)-5-[8-(3-phenylpropionylamino)isoquinolin-4-yl]-1H-indazole-3-carboxilic Intermediate 23.1

4-Bromo-8-nitroisoquinoline

Under argon, at room temperature, 65% HNO$_3$ (200 mmol, 13.85 ml) is added in small portions to a solution of 4-bromoisoquinoline (100 mmol, 21.24 g) in 36N H$_2$SO$_4$ (50 ml). The reaction mixture is stirred for 3 h at room temperature. It is cooled to 0° C. and is then diluted with water. A yellow precipitate forms. It is filtered. The pH of the filtrate is adjusted to pH 10 by slow addition of 5N NaOH. The white precipitate which appears is extracted with CH$_2$Cl$_2$. This organic solution is washed with brine, dried over Na$_2$SO$_4$ and then evaporated under vacuum. The residue is purified by eluting on silica gel with an AcOEt/petroleum ether mixture. The purified product is recrystallized from absolute ethanol (EtOH).

2.71 g of product are obtained in the form of yellow crystals.
m.p.: 127-128° C.

Intermediate 23.2

8-Amino-4-bromoisoquinoline

Tin chloride (SnCl$_2$, 2H$_2$O), 12.04 g, 53.3 mmol) in solution in a mixture of EtOH (30 ml) and 12N HCl (30 ml) is added to a solution of intermediate 23.1 (2.70 g, 10.7 mmol) in EtOH (50 ml). The reaction mixture is heated under reflux for 1 h. After cooling, the orange-coloured precipitate is filtered and then taken up in water. The product is extracted at a basic pH with diethyl ether. The tin salts are removed by filtration on celite. The organic phase is dried over Na$_2$SO$_4$ and then evaporated under vacuum. The residue is recrystallized from absolute EtOH.

2.26 g of product are obtained.
m.p.: 200-201° C.
NMR (DMSO-d6): 6.5 (s, 2H), 6.85 (d, 1H), 7.15 (d, 1H), 7.6 (t, 1H), 8.6 (s, 1H), 9.45 (s, 1H).

Intermediate 23.3

N-(4-Bromoisoquinolin-8-yl)-3-phenylpropionamide

3-Phenylpropionyl chloride (176.5 µl, 1.18 mmol) is added at 0° C. to a solution of intermediate 23.2 (265 mg, 1.18 mmol) in anhydrous THF (20 ml). The stirring is maintained overnight at room temperature. The reaction mixture is evaporated under vacuum and then the residue is extracted with NaHCO$_3$/AcOEt. The organic solution is washed with brine, dried over Na$_2$SO$_4$ and then evaporated under vacuum. The residue is purified on silica gel, eluting with an AcOEt/petroleum ether (2/3) mixture.

340 mg of product are obtained.

m.p.: 174-175° C.

NMR (DMSO-d6): 2.84 (t, J=7.9, 2H), 2.99 (t, J=7.9, 2H), 7.21 (m, 1H), 7.31 (m, 4H), 7.92 (s, 3H), 8.76 (s, 1H), 9.30 (s, 1H), 10.28 (s, 1H).

Intermediate 23.4

N-(Pyridin-4-yl)-5-[8-(3-phenylpropionylamino)isoquinolin-4-yl]-1-(2-trimethylsilylethoxymethyl)-1H-indazole-3-carboxamide Intermediate 23.3 and intermediate 10.3 are coupled under Suzuki conditions in a manner similar to the procedure described in Example 10, on the scale of 0.93 mmol. The crude product is taken up in AcOEt/Et$_2$O and then filtered.

380 mg of product are obtained in the form of a white powder.

N-(Pyridin-4-yl)-5-[8-(3-phenylpropionylamino)isoquinolin-4-yl]-1H-indazole-3-carboxilic The compound is obtained in a manner similar to the procedure described in Example 11 by cleaving the protecting group SEM of intermediate 23.4 (380 mg, 0.59 mmol). The crude product is washed with THF and then with diethyl ether.

150 mg of product are obtained in the form of a yellowish powder.

m.p.: 205° C.

LC/MS/UV: MH+513 (100%)

$^1$H NMR (500 MHz, DMSO-D6) δ (ppm): 2.87 (t, J=6.4, 2H), 3.03 (t, J=6.4, 2H), 7.28 (m, 1H), 7.38 (m, 4H), 7.68 (d, J=8.5, 2H), 7.80 (t, J=8.0, 1H), 7.89 (d, J=7.6, 1H), 7.93 (d, J=8.6, 1H), 7.97 (d, J=5.1, 2H), 8.37 (s, 1H), 8.51 (d, J=5.3, 2H), 9.43 (s, 1H), 10.33 (s, 1H), 10.89 (s, 1H), 14.1 (s, 1H).

EXAMPLE 24

Compound No. 56

N-(Pyridinyl-4-yl)-5-{8-[(pyridine-3-carbonyl)amino]isoquinolin-4-yl}-1H-indazole-3-carboxamide hydrochloride

Intermediate 24.1

N-(4-Bromoisoquinolin-8-yl)nicotinamide

Nicotinoyl chloride hydrochloride (356 mg, 2 mmol) and triethylamine (558 µl, 2 mmol) are added to a solution of 8-amino-4-bromoisoquinoline (intermediate 23.2, 446 mg, 0.90 mmol) in anhydrous THF (25 ml). The reaction mixture is stirred overnight, diluted with AcOEt (200 ml) and washed twice with 1N NaOH (100 ml) and then the organic phase is dried over Na$_2$SO$_4$ and evaporated under vacuum. The residue is purified on silica gel, eluting with AcOEt.

200 mg of product are obtained.

m.p.: 221-222° C.

NMR (DMSO-d6): 7.62 (dd, J=7.6, J=4.4, 1H), 7.96 (dd, J=6.9, J=1.9, 1H), 8.00 (dd, J=8.2, J=8.2, 1H), 8.04 (broad d, J=8.8, 1H), 8.44 (ddd, J=2.2, J=2.2, J=7.6, 1H), 8.80 (s, 1H), 8.81 (dd, J=5.7, J=1.3, 1H), 9.26 (broad d, J=1.9, 1H), 9.48 (s, 1H), 10.95 (s, 1H).

Intermediate 24.2

N-(Pyridinyl-4-yl)-5-{8-[(pyridine-3-carbonyl)amino]isoquinolin-4-yl}-1-(2-trimethylsilylethoxymethyl)-1H-indazole-3-carboxamide Intermediate 24.1 and intermediate 10.3 are coupled under Suzuki conditions in a manner similar to the procedure described in Example 10, on the scale of 0.79 mmol. The crude product is taken up in CH$_3$OH/AcOEt and then filtered. The filtrate is concentrated. The residue is taken up in hot AcOEt and the product obtained is isolated by filtration.

360 mg of product are obtained in the form of a powder.

N-(Pyridinyl-4-yl)-5-{8-[(pyridine-3-carbonyl)amino]-isoquinolin-4-yl}-1H-indazole-3-carboxamide hydrochloride The title compound is obtained in a manner similar to the procedure described in Example 11 by cleaving the protecting group SEM of intermediate 24.2 (360 mg, 0.58 mmol). The crude product is taken up in the hot state in a CH$_2$Cl$_2$/MeOH mixture and filtered. The filtrate is acidified by adding 6N HCl. The precipitate which appears is filtered. The solid is washed with a CH$_3$OH/Et$_2$O mixture.

140 mg of product are obtained in the form of a powder.

m.p.: >250° C.

LC/MS/UV: MH+486 (100%)

$^1$H NMR (500 MHz, DMSO-D6) δ (ppm): 7.70 (dd, J=4.4, J=6.3, 1H), 7.74 (d, J=8.2, 1H), 7.82 (dd, J=5.7, J=3.2, 1H), 7.99 (m, 3H), 8.40 (s, 1H), 8.48 (d, J=6.3, 2H), 8.55 (d, J=8.2, 1H), 8.64 (s, 1H), 8.77 (d, J=6.3, 2H), 8.87 (d, J=3.8, 1H), 9.34 (s, 1H), 9.72 (s, 1H), 11.15 (s, 1H), 11.90 (s, 1H), 14.52 (s, 1H).

EXAMPLE 25

Compound No. 57

N-(Pyridin-4-yl)-5-(8-benzylaminoisoquinolin-4-yl)-1H-indazole-3-carboxamide

Intermediate 25.1

Benzyl(4-bromoisoquinolin-8-yl)amine

Under argon, benzaldehyde (584 µl, 5.75 mmol) is added to a solution of 8-amino-4-bromoisoquinoline (Intermediate 23.2, 1.11 g, 5 mmol) in absolute EtOH (60 ml). The mixture is heated at 90° C. for 24 h. It is cooled to 0° C. and then sodium cyanoborohydride (NaBH$_3$CN, 3.3 g, 50 mmol) is added in small portions. The stirring is maintained for 2 h at room temperature. The reaction mixture is diluted with AcOEt (600 ml) and is then washed with water. The organic phase is dried over Na$_2$SO$_4$ and then evaporated. The residue is purified on silica gel, eluting with an AcOEt/petroleum ether (1/4) mixture.

640 mg of product are obtained.

m.p.: 193-194° C.

¹H NMR (500 MHz, DMSO-D6) δ (ppm): 4.54 (d, J=5.7, 2H), 6.60 (d, J=8.2, 1H), 7.18 (d, J=8.2, 1H), 7.23 (dd, J=7.2, J=7.2, 1H), 7.32 (dd, J=7.9, J=7.9, 2H), 7.41 (d, J=7.9, 2H), 7.56 (dd, J=8.2, J=8.2, 1H), 7.79 (t, J=6.0, 1H), 8.64 (s, 1H), 9.62 (s, 1H).

Intermediate 25.2

N-(Pyridin-4-yl)-5-(8-benzylaminoisoquinolin-4-yl)-1-(2-trimethylsilylethoxymethyl)-1H-indazole-3-carboxamide Intermediate 25.1 and intermediate 10.3 are coupled under Suzuki conditions in a manner similar to the procedure described in Example 10, on the scale of 0.91 mmol. The crude product is crystallized from CHCl$_3$/Et$_2$O.

510 mg of product are obtained in the form of a yellow powder.

N-(Pyridin-4-yl)-5-(8-benzylaminoisoquinolin-4-yl)-1H-indazole-3-carboxamide

This compound is obtained in a manner similar to the procedure described in Example 11 by cleaving the protecting group SEM of Intermediate 25.2 (510 mg, 0.85 mmol). The crude product is taken up in MeOH. The mixture is stirred for 30 min. The solid is filtered, washed with MeOH and then with diethyl ether.

60 mg of product are obtained in the form of a powder.

m.p. >250° C.

LC/MS/UV: MH+471 (94.8%)

¹H NMR (500 MHz, DMSO-D6) δ (ppm): 4.47 (d, J=5.5, 1H), 6.53 (d, J=8.2, 1H), 6.91 (d, J=8.2, 1H), 7.23 (d, J=7.2, 1H), 7.34 (t, J=7.2, 2H), 7.39 (t, J=7.2, 1H), 7.45 (d, J=7.2, 2H), 7.56 (d, J=8.2, 1H), 7.71 (t, J=5.3, 1H), 7.83 (d, J=8.8, 1H), 7.91 (d, J=5.0, 2H), 8.27 (s, 1H), 8.40 (s, 1H), 8.45 (d, J=5.0, 2H), 9.70 (s, 1H), 10.80 (s, 1H), 13.92 (s, 1H).

EXAMPLE 26

Compound No. 59

N-(Pyridin-4-yl)-5-[5-(3-phenylpropionylamino)isoquinolin-4-yl]-1H-indazole-3-carboxamide Intermediate 26.1

4-Bromo-5-nitroisoquinoline

The nitration of 4-bromoisoquinoline allows the synthesis of 4-bromo-8-nitroisoquinoline (Intermediate 23.1) and of 4-bromo-5-nitroisoquinoline. The yellow precipitate which forms after addition of H$_2$O (see synthesis of Intermediate 23.1) is taken up in AcOEt. The solution is washed with a 10% aqueous NaHCO$_3$ solution and then with brine. The crude product obtained after drying over Na$_2$SO$_4$ and evaporation under vacuum is recrystallized from absolute EtOH.

22.35 g of product are obtained in the form of crystals.

m.p. 174-175° C.

Intermediate 26.2

5-Amino-4-bromoisoquinoline

This compound is obtained in a manner similar to Intermediate 23.2, from Intermediate 26.1, on the scale of 25 mmol. The crude product is recrystallized from absolute EtOH.

5.11 g of product are obtained in the form of yellow crystals.

m.p.: 156-157° C.

¹H NMR (500 MHz, DMSO-D6) δ (ppm): 6.18 (s, 2H), 7.08 (d, 1H), 7.37 (d, 1H), 7.48 (dd, 1H), 8.4 (s, 1H), 9.0 (s, 1H).

Intermediate 26.3

N-(4-Bromoisoquinolin-5-yl)-3-phenylpropionamide

This compound is prepared from Intermediate 26.2, in a manner similar to Intermediate 23.3, on the scale of 1.6 mmol. The crude product is purified on silica gel, eluting with an AcOEt/methylene chloride (1/5) mixture.

470 mg of product are obtained.

m.p.: 168-169° C.

¹H NMR (500 MHz, DMSO-D6) δ (ppm): 2.75 (t, 2H), 2.95 (t, 2H), 7.3 (m, 5H), 7.55 (d, 1H), 7.8 (t, 1H), 8.18 (d, 1H), 8.67 (s, 1H), 9.35 (s, 1H), 10.0 (s, 1H).

Intermediate 26.4

N-(Pyridin-4-yl)-5-[5-(3-phenylpropionylamino)isoquinolin-4-yl]-1-(2-trimethylsilylethoxymethyl)-1H-indazole-3-carboxamide Intermediate 26.3 and Intermediate 10.3 are coupled under Suzuki conditions in a manner similar to the procedure described in Example 10, on the scale of 1 mmol. The reaction is carried out in a mixture of DME (6 ml) and DMSO (1 ml). The reaction mixture is diluted with AcOEt/H$_2$O and then filtered. The organic phase is separated, dried over Na$_2$SO$_4$ and then evaporated. The crude product is purified on silica gel, eluting with an AcOEt/MeOH (98/2) mixture.

600 mg of product are obtained in the form of a cream-coloured solid.

N-(Pyridin-4-yl)-5-[5-(3-phenylpropionylamino)isoquinolin-4-yl]-1H-indazole-3-carboxamide This compound is obtained in a manner similar to the procedure described in Example 11 by cleaving the protecting group SEM of Intermediate 26.4 (600 mg, 0.93 mmol). The reaction mixture is heated for 3 days at 60° C. The reaction mixture is diluted with water and then filtered. The solid obtained by filtration is recrystallized from isopropanol, and then dried under vacuum at 90° C.

260 mg of product are obtained.

m.p.: 209-211° C.

LC/MS/UV: MH+513 (99.4%)

¹H NMR (500 MHz, DMSO-D6) δ (ppm): 1.41 (m, 1H), 1.50 (m, 1H), 2.22 (m, 1H), 2.33 (M, 1H), 6.81 (d, J=7.6, 1H), 7.11 (t, J=7.7, 1H), 7.18 (t, J=7.7, 2H), 7.34 (d, J=8.8, 1H), 7.59 (d, J=7.6, 1H), 7.71 (d, J=8.8, 1H), 7.76 (t, J=8.0, 1H), 7.93 (d, J=5.7, 2H), 8.17 (d, J=8.2, 1H), 8.22 (s, 1H), 8.31 (s, 1H), 8.45 (d, J=5.7, 2H), 9.00 (s, 1H), 9.38 (s, 1H), 10.80 (s, 1H), 14.02 (s, 1H).

EXAMPLE 27

Compound No. 65

N-(Pyridin-4-yl)-5-(2H-tetrazol-5-yl)-1H-indazole-3-carboxamide hydrochloride

A suspension of the hydrochloride of the compound obtained in Example 19, salified according to a method known to a person skilled in the art, (N-(pyridin-4-yl)-5-cyano-1H-indazole-3-carboxamide hydrochloride, 330 mg, 1.1 mmol), ammonium chloride (615 mg, 11.5 mmol) and sodium azide (715 mg, 11 mmol) in DMF (20 ml) is heated under argon at 115° C. overnight. After cooling, acetic acid (0.7 ml) is added and then the reaction mixture is concentrated under vacuum. The residue is taken up in AcOEt/H$_2$O, stirred for 10 min and then filtered. The solid thus separated is suspended in DMF and acidified with 1N HCl. Heating to 80° C. and addition of H$_2$O cause the dissolution of the solid. After cooling, the suspension is filtered to give the expected product.

21 g of product are obtained in the form of a white powder.
m.p.: >250° C.
LC/MS/UV: MH+307 (100%)
$^1$H NMR (500 MHz, DMSO-D6) δ (ppm): 7.93 (d, J=8.2 Hz, 1H), 7.94 (s, 1H) 8.18 (m, 3H) 8.62 (d, J=6.3 Hz, 2H), 9.00 (s, 1H) 11.34 (s, 1H) 14.39 (s, 1H).

EXAMPLE 28

Compound No. 67

N-(Pyridin-4-yl)-5-(1,3-thiazol-5-yl)-1H-indazole-3-carboxamide

Intermediate 28.1

N-Pyridin-4-yl-5-(1,3-thiazol-5-yl)-(2-trimethylsilylethoxymethyl)-1H-indazole-3-carboxamide Under an argon atmosphere, a solution of 2-trimethylsilyl (thiazole) (1.97 ml, 12 mmol) in anhydrous diethyl ether (12 ml) is added dropwise to a solution of n-butyllithium (8.25 ml, 1.6N in hexane, 13.2 mmol) in anhydrous diethyl ether (12 ml) cooled to −78° C. The stirring is maintained for 30 min at −78° C. and a molar solution of ZnCl$_2$ (4.91 g, 36 mmol) in anhydrous diethyl ether (36 ml) freshly prepared from very dry ZnCl$_2$ is added. The cooling bath is removed and the mixture is stirred for 30 min at room temperature. The solvents are evaporated under vacuum. Under argon, a mixture of Intermediate 9.3 (5.37 g, 12 mmol) and tetrakis(triphenylphosphine)palladium (277 mg) in anhydrous THF (50 ml) is added to the residue and the suspension is heated under reflux for 24 h. The reaction mixture is acidified to pH 2 by adding 1N HCl and is then concentrated under vacuum. 1N sodium hydroxide is added in order to obtain pH 10. The solid obtained is stirred in the presence of CH$_2$Cl$_2$ and the zinc salts are separated by filtration. The filtrate is washed with water. The organic phase is dried over MgSO$_4$ and then evaporated. The brown oil obtained (5.10 g) is rapidly filtered on silica. After crystallization from diethyl ether, a yellow solid (2.40 g) is obtained. The solid is chromatographed on silica (300 g). An elution gradient petroleum ether/AcOEt (2/3) to petroleum ether/AcOEt (1.3) makes it possible to separate two isomers. The expected compound is more polar.

1.08 g of product are obtained in the form of a white powder.

N-Pyridin-4-yl-5-(1,3-thiazol-5-yl)-1H-indazole-3-carboxamide

This compound is obtained in a manner similar to Example 11 by cleaving the protecting group SEM of Intermediate 28.1 (452 mg, 1 mmol). The crude product is recrystallized from an MeOH/AcOEt mixture in the presence of a trace of water and is then filtered.

22.5 g of product are obtained in the form of a yellow solid.
m.p.: >250° C.
LC/MS/UV: MH+322 (98.5%)

$^1$H NMR (500 MHz, DMSO-D6) δ (ppm): 7.77 (d, J=8.8 Hz, 1H) 7.86 (d, J=8.8 Hz, 1H) 7.93 (d, J=6.3 Hz, 3H) 8.35 (s, 1H) 8.41 (s, 1H) 8.47 (d, J=6.3 Hz, 2H) 9.10 (s, 1H) 10.80 (s, 1H), 14.0 (s, 1H)

EXAMPLE 29

Compound No. 68

N-(Pyridin-4-yl)-5-(1H-pyrrolo[2,3-c]pyridin-4-yl)-1H-indazole-3-carboxamide

Intermediate 29.1

3-Nitropyridin-4-ol

A nitric acid solution (HNO$_3$>90%, 13.3 ml) is slowly added to a solution of oleum (H$_2$SO$_4$ containing 20% SO$_3$, d=1.9, 10.5 ml) cooled to 0° C. 4-Pyridol nitrate (10 g, 63 mmol) is added at 0° C. to the mixture which is then heated at 90° C. for 1 h 30 min. The reaction mixture is poured over 50 g of ice. The suspension is stirred for 30 min at 0° C. and is then filtered. The solid is washed with a few ml of water and then air-dried.

6.59 g of product are obtained in the form of a white powder.

Intermediate 29.2

3-Bromo-5-nitropyridin-4-ol

Bromine (5.07 g. 31.7 mmol) is added dropwise to a suspension of Intermediate 29.1 (4.04 g, 28.4 mmol) in H$_2$O (40 ml). The mixture is heated with an oil bath at a temperature of 90° C. for 1 h. After cooling, the mixture is filtered. The solid is washed with H$_2$O and then dried in a desiccator in the presence of silica gel.

4.51 g of product are obtained in the form of a white solid.

Intermediate 29.3

3-Bromo-4-chloro-5-nitropyridine

Intermediate 29.2 (5.30 g, 24.0 mmol) is dried at 60° C. under vacuum (0.5 mBar) for 2 h in a two-necked flask. PCl$_5$ (9.12 g, 43.8 mmol) and POCl$_3$ (0.5 ml, 5.4 mmol) are added. The mixture is heated at 160° C. in an oil bath. After 20 min, the solid was converted to a clear brown oil. After cooling, the mixture solidifies. The volatile substances are evaporated under vacuum and then the solid suspended in CHCl$_3$ is treated at 0° C. with an aqueous potassium acetate solution (AcOK 25 g/35 ml H$_2$O). The organic phase is separated and is then evaporated. The residue is extracted with a diethyl ether/NaHCO$_3$ mixture. The organic phase is washed with brine, dried over Na$_2$SO$_4$ and evaporated. The residue is taken up in CH$_2$Cl$_2$. The insolubles are removed by filtration and the filtrate is evaporated to give the expected product.

4.66 g of product are obtained in the form of a brown oil.

Intermediate 29.4

Diethyl (3-bromo-5-nitropyridin-4-yl)malonate

Under nitrogen, diethyl malonate (7.2 ml, 47.4 mmol) is added over 10-15 min to a suspension of NaH (1.70 g, 55-60% in oil, 39-46 mmol) in anhydrous DMF (30 ml), such that the temperature of the reaction mixture does not exceed 50° C. The stirring is maintained for a further 30 min after the addition. Intermediate 29.3 (4.46 g, 18.62 mmol) is added in solid form in small portions. The stirring is maintained for 3 h 30 min at room temperature. Water (50 ml) and AcOH (5 ml) are added. The mixture is extracted with diethyl ether. The organic phase is washed with brine, dried over $Na_2SO_4$ and evaporated. The residue is eluted on silica gel (300 g) according to a gradient from an AcOEt/petroleum ether (1/9) mixture to an AcOEt/petroleum ether (3/7) mixture.

5.15 g of product are obtained in the form of a brown oil.

Intermediate 29.5

3-Bromo-4-methyl-5-nitropyridine

Intermediate 29.4 (5.15 g, 14.2 mmol) is heated at 100° C. in the presence of 18% aqueous HCl (50 ml) for 15 h. The mixture is extracted with diethyl ether (3×80 ml). The ethereal solution is washed with brine, dried over $MgSO_4$ and evaporated under vacuum to give the expected product.

2.43 g of product are obtained in the form of a yellow solid.

Intermediate 29.6

2-(3-Bromo-5-nitropyridin-4-yl)-N,N-dimethylethyleneamine

A mixture of intermediate 29.5 (1.136 g, 5.19 mmol) and diethyl acetal of DMF (1.46 ml, 8.52 mmol) in DMF (6 ml) is heated at 85° C. for 1 h 15 min. The DMF is evaporated under vacuum to give the expected product.

1.407 g of product are obtained in the form of a purple-coloured solid.

Intermediate 29.7

4-Bromo-1H-pyrrolo[2,3-c]pyridine

Intermediate 29.6 (1.407 g, 5.13 mmol) in solution in acetic acid (15 ml) is heated under nitrogen in the presence of iron (powder 325 mesh, 1.85 g, 33.1 mmol) at 120° C. for 40 min. The mixture is filtered. The iron salts are washed with AcOH (5 ml). The filtrate is diluted in 75 ml of water to give a clear orange-red coloured solution. This solution is neutralized by adding solid $K_2CO_3$ until a pH of 9 is obtained. The brownish suspension is extracted with $CHCl_3$. The organic solution is washed with brine, filtered on a 0.45 μM membrane, dried over $Na_2SO_4$ and is finally evaporated under vacuum.

801 mg of product are obtained in the form of a brown-grey solid.

Intermediate 29.8

N-(Pyridin-4-yl)-5-(1H-pyrrolo[2,3-c]pyridin-4-yl)-1-(2-trimethylsilylethoxymethyl)-1H-indazole-3-carboxamide The synthesis of this intermediate is carried out in a manner similar to the synthesis of Intermediate 10.4, carrying out a Suzuki reaction between Intermediate 29.7 and Intermediate 10.3 on the scale of 2.43 mmol. The crude product is purified on silica gel (50 g), eluting with an AcOEt/MeOH (95/5) mixture.

780 mg of product are obtained in the form of a white powder.

N-(Pyridin-4-yl)-5-(1H-pyrrolo[2,3-c]pyridin-4-yl)-1H-indazole-3-carboxamide

This compound is obtained in a manner similar to Example 11 by cleaving the protecting group SEM of Intermediate 29.8 (780 mg, 1.61 mmol) with TFA followed by heating in the presence of ethylenediamine. The crude product is stirred for 1 h in the presence of MeOH and is then filtered.

480 mg of product are obtained in the form of a white powder.

m.p.: >250° C.

LC/MS/UV: MH+355 (100%)

$^1$H NMR (500 MHz, DMSO-D6) δ (ppm): 6.67 (s, 1H) 7.71 (s, 1H) 7.84 (s, 2H) 7.93 (d, J=5.7 Hz, 2H) 8.27 (s, 1H) 8.46 (d, J=6.3 Hz, 2H) 8.55 (s, 1H) 8.77 (s, 1H) 10.79 (s, 1H) 11.80 (s, 1H) 12-14 (s, 1H)

EXAMPLE 30

Compound No. 74

5-(5-Amino-4-methylpyridin-3-yl)-N-pyridin-4-yl-1H-indazole-3-carboxamide

Intermediate 30.1

3-Bromo-4-methyl-5-aminopyridine

This compound is obtained by reducing 3-bromo-4-methyl-5-nitropyridine (Intermediate 29.5) with iron in a manner similar to the synthesis of Intermediate 29.7, on the scale of 10 mmol.

1.20 g of product are obtained in the form of a cream-coloured solid.

Intermediate 30.2

5-(5-Amino-4-methylpyridin-3-yl)-N-pyridin-4-yl-1-(2-trimethylsilylethoxymethyl)-1H-indazole-3-carboxamide The synthesis of this intermediate is carried out in a manner similar to the synthesis of Intermediate 10.4, by carrying out a Suzuki reaction between Intermediate 30.1 and Intermediate 10.3 on the scale of 2.48 mmol. The reaction mixture is evaporated. The residue is taken up in $AcOEt/H_2O$. An insoluble product is separated. After stirring for 1 h, it is filtered.

1.02 g of product are obtained in the form of a cream-coloured powder.

5-(5-Amino-4-methylpyridin-3-yl)-N-pyridin-4-yl-1H-indazole-3-carboxamide

Intermediate 30.2 (980 mg, 2.06 mmol) in solution in THF (30 ml) is reacted with a solution of tetrabutylammonium fluoride (1M solution in THF, 10.3 ml), ethylenediamine (0.347 ml, 5.2 mmol) and $H_2O$ (0.377 ml). The mixture is heated at 60° C. for 3 days and then evaporated. The residue is stirred in an $AcOEt/H_2O$ mixture and then filtered. The solid thus recovered is stirred in the presence of MeOH and is then filtered to give the expected product (270 mg) in the form of a cream-coloured solid. The filtrate is evaporated under vacuum and is then chromatographed on silica gel (50 g), eluting with an $MeOH/CH_2Cl_2$ (1/4) mixture to give a $2^{nd}$ batch of the expected product (1.5 g) in the form of a yellow solid.

LC/MS/UV: MH+345 (100%)

¹H NMR (500 MHz, DMSO-D6) δ (ppm): 1.98 (s, 3H) 5.19 (s, 2H) 7.40 (d, J=8.2 Hz, 1H) 7.67 (s, 1H) 7.74 (d, J=8.8 Hz, 1H) 7.91 (d, J=6.3 Hz, 2H) 7.96 (s, 1H) 8.08 (s, 1H) 8.45 (d, J=6.3 Hz, 2H) 10.76 (s, 1H) 13.67 (s, 1H)

EXAMPLE 31

Compound No. 70

5-(1H-Pyrazol-4-yl)-N-(pyridin-4-yl)-1H-indazole-3-carboxamide

Intermediate 31.1

4-Iodo-1-(2-trimethylsilylethoxymethyl)-1H-pyrazole

Under argon, diisopropylethylamine (DIEA, 1.75 ml, 10 mmol) and trimethylsilylethoxymethyl chloride (SEMCl, 1.83 ml, 10 mmol) are added to a solution of 4-iodopyrazole (1.94 g, 10 mmol) in $CH_2Cl_2$ (100 ml). The mixture is stirred overnight at room temperature. The solvent is evaporated under vacuum. The residue is taken up in a diethyl ether/water mixture. The organic phase after drying and evaporation gives a colourless oil which is purified by eluting on silica gel with an $AcOEt/CH_2Cl_2$ (5/95) mixture.

3.02 g of product are obtained in the form of a colourless oil.

Intermediate 31.2

N-(Pyridin-4-yl)-1-(2-trimethylsilylethoxymethyl)-5-(1-(2-trimethylsilylethoxymethyl)-1H-pyrazol-4-yl)-1H-indazole-3-carboxamide The synthesis of this intermediate is carried out in a manner similar to the synthesis of Intermediate 10.4 by carrying out a Suzuki reaction between Intermediate 31.1 and Intermediate 10.3 on the scale of 2.0 mmol. The crude product is purified on silica gel (50 g), eluting with an $MeOH/CH_2Cl_2$ (2/98) mixture. The purified compound is crystallized from a $CHCl_3/Et_2O$ mixture.

367 mg of product are obtained in the form of a white powder.

5-(1H-Pyrazol-4-yl)-N-(pyridin-4-yl)-1H-indazole-3-carboxamide

This compound is obtained in a manner similar to Example 11 by cleaving the protecting groups SEM of Intermediate 31.2 (550 mg, 0.97 mmol) with TFA followed by heating in the presence of ethylenediamine. The reaction mixture is filtered. The solid is stirred in the presence of $CHCl_3/H_2O$. The insoluble fraction is stirred in the presence of MeOH for 1 h and then filtered to give the expected product.

220 mg of product are obtained in the form of a white powder.

m.p.: >250° C.

LC/MS/UV: MH+305 (100%)

¹H NMR (500 MHz, DMSO-D6) δ (ppm): 7.67 (d, J=8.2 Hz, 1H) 7.75 (d, J=6.9 Hz, 1H) 7.94 (d, J=6.3 Hz, 2H) 7.96 (broad s, 1H) 8.21 (broad s, 1H) 8.35 (s, 1H) 8.46 (d, J=5.7 Hz, 2H) 10.72 (s, 1H) 13.0 (s, 1H)

EXAMPLE 32

Compound No. 72

5-(1,3-Oxazol-5-yl)-N-(pyridin-4-yl)-1H-indazole-3-carboxamide

Intermediate 32.1

5-Formyl-N-(pyridin-4-yl)-1-(2-trimethylsilylethoxymethyl-1H-indazole-3-carboxamide A carbon monoxide stream is introduced over 15 min into a solution of Intermediate 9.3 (4.95 g, 10 mmol) in THF (50 ml). Tetrakis(triphenylphosphine)palladium (578 mg, 0.5 mmol) is added and then a carbon monoxide stream is introduced over 10 min. The mixture is heated to 50° C. and a tributyltin hydride solution (3.05 ml, 11 mmol) in THF (20 ml) is slowly added over 2 h 30 min. After cooling, water (0.5 ml) is added and the reaction mixture is evaporated. The residue is purified on silica gel, eluting with $MeOH/AcOEt/CH_2Cl_2$ (2/29/69).

2.65 g of product are obtained in the form of a yellow solid.

Intermediate 32.2

5-(1,3-Oxazol-5-yl)-N-(pyridin-4-yl)-1-(2-trimethylsilylethoxymethyl)-1H-indazole-3-carboxamide $K_2CO_3$ (1.02 g, 7.35 mmol) and tosylmethyl isocyanate (TosMIC, 1.44 g, 7.35 mmol) are added to Intermediate 32.1 (2.65 g, 6.68 mmol) in solution in MeOH (100 ml). The mixture is heated under reflux for 2 h 30 min, and then after cooling is concentrated under vacuum. The residue is taken up in $AcOEt/H_2O$. After drying and evaporation, the organic phase gives a solid which is purified on silica gel, eluting with $MeOH/AcOEt/CH_2Cl_2$ (3/28.5/68.5). The purified product is recrystallized from AcOEt.

2.345 g of product are obtained in the form of a white solid.

5-(1,3-Oxazol-5-yl)-N-(pyridin-4-yl)-1H-indazole-3-carboxamide

Intermediate 32.2 (360 mg, 0.82 mmol) is reacted at room temperature with TFA (3 ml) for 1 h. The reaction mixture is evaporated under vacuum. The residue is taken up in THF, causing the separation of a solid. The mixture is again evaporated and then taken up in THF (10 ml). Ethylenediamine (267 µl, 4 mmol) is added and the mixture is heated at 70° C. overnight. The THF is evaporated. The residue is triturated in MeOH, filtered and then washed with diethyl ether. It is taken up in 80 ml of an $MeOH/H_2O$ (9/1) mixture. The mixture is heated under reflux. DMF is added until complete dissolution is obtained. After cooling, an orange-coloured solid appears which is filtered and dried under high vacuum for 2 days.

206 mg of product are obtained in the form of an orange-coloured powder.

LC/MS/UV: MH+306 (94.3%)

¹H NMR (500 MHz, DMSO-D6) δ (ppm): 7.74 (s, 1H) 7.77 (d, J=8.8 Hz, 1H) 7.84 (d, J=8.8 Hz, 1H) 7.92 (d, J=5.7 Hz, 2H) 8.45 (d, J=5.0 Hz, 3H) 8.46 (s, 1H) 8.51 (s, 1H) 10.82 (s, 1H) 13.9 (s, 1H)

EXAMPLE 33

Compound No. 73

N-{3-[(Ethylamino)methyl]phenyl}-5-isoquinolin-4-yl-1H-indazole-3-carboxamide dihydrochloride Intermediate 33.1

N-(3-Nitrobenzyl)ethaneamine hydrochloride

Under argon, a BH₃-THF solution (1M, 60 ml) is added dropwise to a solution of N-(3-nitrobenzyl)acetamide (3.89 g, 20 mmol) in anhydrous THF (100 ml). The reaction mixture is stirred at 40° C. overnight. MeOH (40 ml) is added. The solvents are evaporated under vacuum and the residue is heated for 4 h at 60° C. in a THF/4N HCl (80/25) mixture. After cooling, a solid separates. AcOEt (50 ml) is added, while the stirring is maintained. The solid is filtered, washed with AcOEt and diethyl ether and then dried.

3.95 g of product are obtained in the form of a white powder.

Intermediate 33.2

(3-Aminobenzyl)ethylamine

Under argon, Intermediate 33.1 (3.90 g, 18 mmol) in glacial acetic acid (100 ml) is stirred at 110° C. for 30 min in the presence of iron (6.64 g, 118.8 mmol). After cooling, the iron salts are filtered and washed with acetic acid (15 ml). The filtrate is diluted in water (200 ml) and then brought to pH 9 by adding solid K₂CO₃ and to pH 12 by adding NaOH. The resulting suspension is extracted with CH₂Cl₂. The organic solution is dried and then evaporated to give the expected product.

2.65 g of product are obtained in the form of a yellow oil.

Intermediate 33.3 tert-Butyl (3-aminobenzyl)ethylcarbamate

Under argon, Intermediate 33.2 (2.60 g, 17.3 mmol) in solution in CH₂Cl₂ (150 ml) is reacted with di-tert-butyl dicarbonate (3.89 g, 17.3 mmol) for 1 h 30 min. The solvent is evaporated. The oil obtained is purified on silica gel, carrying out an elution gradient from an AcOEt/CH₂Cl₂ (1/9) mixture to an AcOEt/CH₂Cl₂ (1/4) mixture.

1.28 g of product are obtained in the form of a colourless gum.

Intermediate 33.4 tert-Butyl (3-{[(5-Bromo-1-(2-trimethylsilylethoxymethyl)-1H-indazol-3-yl)carbonyl]amino}benzyl)ethylcarbamate Under argon, a solution of isopropyl chloroformate in toluene (1M, 5.5 ml, 5.5 mmol) is added at 0° C. to a solution of 5-bromo-1-(2-trimethylsilylethoxymethyl)-1H-indazole-3-carboxylic acid (1.86 g, 5 mmol), prepared from 5-bromoisatin in a manner similar to Intermediate 9.2, in anhydrous THF (45 ml), followed by N-methylmorpholine (600 µl, 5.5 mmol). The mixture is stirred for 20 min at 0° C. and then for 15 min at room temperature. After cooling to 0° C., Intermediate 33.3 (1.38 g, 5.5 mmol) in solution in anhydrous THF (5 ml) is added. The reaction mixture is stirred for 5 h at room temperature and is then concentrated under vacuum. The residue is taken up in AcOEt/H₂O. The organic phase is washed with 10% K₂CO₃, dried and then evaporated under vacuum.

2.81 g of product are obtained in the form of a yellow gum.

Intermediate 33.5 tert-Butyl ethyl(3-{[(5-isoquinolin-4-yl-1-(2-trimethylsilylethoxymethyl)-1H-indazol-3-yl)carbonyl]amino}benzyl)carbamate Isoquinolin-4-ylboronic acid (461 mg, 2 mmol) and an aqueous Na₂CO₃ solution (2M, 5 ml, 10 mmol) are added to a solution of Intermediate 33.4 (1.21 g, 2 mmol) in DME (12 ml). The reaction mixture is degassed with argon and then tetrakis(triphenylphosphine)palladium (116 mg, 0.1 mmol) is added. After degassing again, the mixture is heated at 80° C. for 20 h. The reaction mixture is evaporated under vacuum and then taken up in AcOEt/H₂O and filtered. The AcOEt solution is dried and then evaporated under vacuum. The residue is purified on silica gel, eluting with an AcOEt/DCM (1/3) mixture.

1.08 g of product are obtained in the form of a yellow gum.

N-{3-[(Ethylamino)methyl]phenyl}-5-isoquinolin-4-yl-1H-indazole-3-carboxamide dihydrochloride Under argon, TFA (20 ml) cooled to 4° C. is added to Intermediate 33.5 (1.0 g, 1.53 mmol). The mixture is stirred for 2 h at room temperature. The TFA is evaporated under vacuum. The residue is taken up in toluene and then the mixture is evaporated under vacuum. This operation is repeated. The residue is taken up in THF (50 ml). Ethylenediamine (620 µl, 9.20 mmol) is added and the mixture is heated at 70° C. under argon overnight. The mixture is evaporated and the residue is extracted with AcOEt/H₂O. The organic phase, after drying and evaporation, gives a compound which is solubilized in an isopropanol/4N HCl (20 ml/2 ml) mixture. The solid which slowly separates is filtered.

622 mg of product are obtained in the form of a yellow solid.

LC/MS/UV: MH+422 (100%)

¹H NMR (500 MHz, DMSO-D6) δ (ppm): 1.21 (t, J=6.9 Hz, 3H) 2.95 (m, 2H) 4.09 (t, J=6.0 Hz, 2H) 7.30 (d, J=7.6 Hz, 1H) 7.40 (t, J=7.9 Hz, 1H) 7.68 (d, J=10.1 Hz, 1H) 7.81 (d, J=8.2 Hz, 1H) 7.92 (d, J=8.2 Hz, 1H) 7.97 (t, J=7.9 Hz, 1H) 8.07 (m, 1H) 8.12 (s, 1H) 8.41 (s, 1H) 8.53 (d, J=7.6 Hz, 1H) 8.67 (s, 1H) 9.1 (broad s, 2H) 9.78 (s, 1H) 10.55 (s, 1H) 14.2 (s, 1H).

The table which follows illustrates the chemical structures and the physical properties of a few compounds of the invention.

In this table:
- in the "salt" column, "-" represents a compound in free base form; whereas "HCl" represents a compound in hydrochloride form and "CH₃SO₃H" represents a compound in the form of a methanesulphonic acid salt. The ratio in brackets is the (acid:base) ratio;
- m.p. (° C.) represents the melting point of the compound in degrees Celsius;
- M+H represents the mass of the compound plus 1;
- "dec." means decomposition of the product.

TABLE

Structure (I): 5-R₁-1H-indazole-3-carboxamide with N-H-(CH₂)n-Ar

| No. | R₁ | n | Ar | Salt | M + H | m.p. (° C.) |
|---|---|---|---|---|---|---|
| 1. | H | 3 | 1-methylimidazol-2-yl | — | 270 | 154-155 |
| 2. | H | 2 | 1H-indol-3-yl | — | 305 | 197-198 |
| 3. | H | 0 | 4-(SO₂NH₂)phenyl | — | 317 | >250 |
| 4. | H | 0 | 4-(PhNH)phenyl | — | 329 | 218 |
| 5. | H | 0 | isoquinolin-5-yl | — | 289 | >250 |
| 6. | H | 0 | 1H-indazol-5-yl | — | 278 | >250 |
| 7. | H | 0 | 4-bromophenyl | — | 316 | >250 |
| 8. | H | 0 | 3-bromophenyl | — | 316 | 229-230 |
| 9. | H | 0 | 2-cyanophenyl | — | 263 | 251-252 |
| 10. | H | 0 | 3-methoxyphenyl | — | 268 | 180 |

TABLE-continued (I)

R₁—[5-indazole]—C(O)NH—(CH₂)nAr

| No. | R₁ | n | Ar | Salt | M + H | m.p. (°C.) |
|---|---|---|---|---|---|---|
| 11. | H | 0 | 4-(ethoxycarbonyl)phenyl | — | 310 | 227-228 |
| 12. | H | 0 | 3-(ethoxycarbonyl)phenyl | — | 310 | 187-188 |
| 13. | H | 0 | 3-carboxyphenyl | — | 282 | >250 |
| 14. | H | 0 | 4-carboxyphenyl | — | 282 | >250 |
| 15. | H | 0 | pyridin-3-yl | CH₃SO₃H (1/1) | 239 | >250 |
| 16. | H | 0 | pyridin-4-yl | HCl (1/1) | 239 | >250 |
| 17. | H | 0 | pyrazin-2-yl | — | 240 | >220 |
| 18. | H | 0 | 6-methoxypyridin-3-yl | — | 269 | 217-218 |
| 19. | H | 0 | 2,4-dimethylquinolin-? | — | 303 | >250 |

TABLE-continued
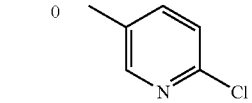
(I)
| No. | R₁ | n | Ar | Salt | M + H | m.p. (° C.) |
|---|---|---|---|---|---|---|
| 20. | H | 0 | 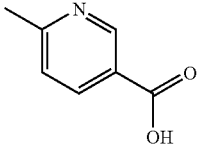 | — | 273 | >250 |
| 21. | H | 0 | 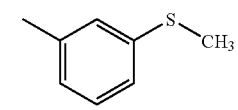 | — | 283 | >250 |
| 22. | H | 0 | 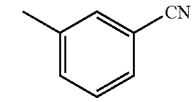 | — | 284 | 188 |
| 23. | H | 0 | 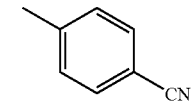 | — | 263 | 242 |
| 24. | H | 0 | 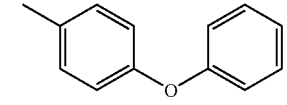 | — | 263 | >250 |
| 25. | H | 0 | 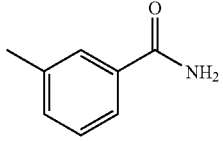 | — | 330 | 206 |
| 26. | H | 0 | 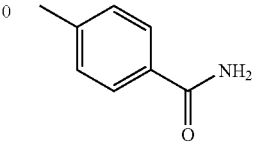 | — | 281 | >250 |
| 27. | H | 0 | 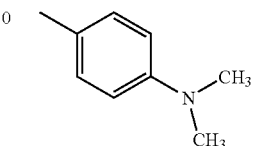 | — | 281 | >250 |
| 28. | H | 0 |  | — | 281 | >250 |

TABLE-continued
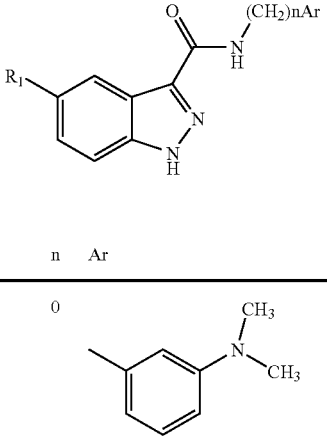
(I)
| No. | R₁ | n | Ar | Salt | M + H | m.p. (° C.) |
|---|---|---|---|---|---|---|
| 29. | H | 0 | 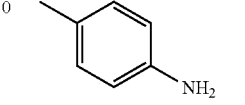 | — | 281 | 191 |
| 30. | H | 0 | 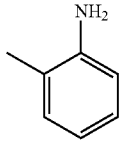 | — | 253 | 236 |
| 31. | H | 0 | 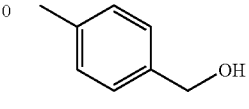 | — | 253 | 185 |
| 32. | H | 0 | 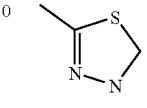 | — | 268 | 243 |
| 33. | H | 0 | 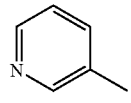 | — | 246 | >250 |
| 34. | 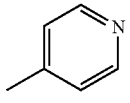 | 0 | 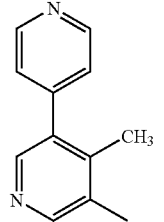 | HCl (1/1) | 316 | 196 |
| 35. | 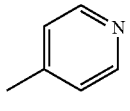 | 0 | 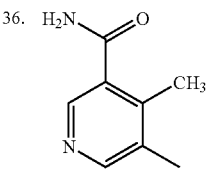 | HCl (1/1) | 407 | 192 |
| 36. | 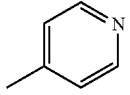 | 0 |  | — | 373 | >250 |

TABLE-continued
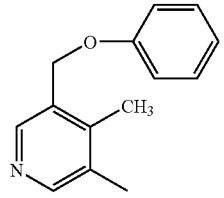
(I)
| No. | R₁ | n | Ar | Salt | M + H | m.p. (° C.) |
|---|---|---|---|---|---|---|
| 37. | 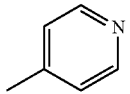 | 0 | 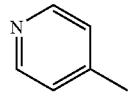 | HCl (1/1) | 436 | 160 |
| 38. | 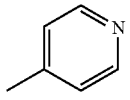 | 0 | 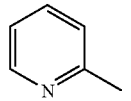 | — | 316 | 192 |
| 39. | 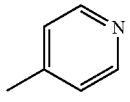 | 0 | 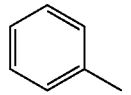 | — | 316 | >250 |
| 40. | 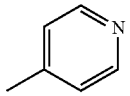 | 0 | 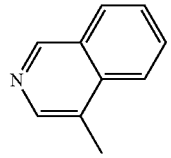 | — | 315 | >250 |
| 41. | 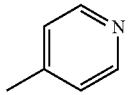 | 0 | 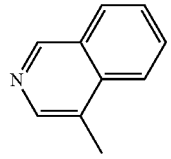 | — | 366 | >250 |
| 42. | 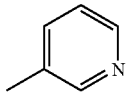 | 1 | 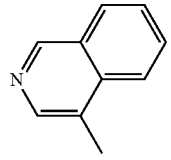 | — | 380 | 238 |
| 43. | 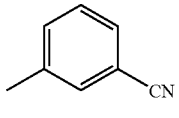 | 0 | 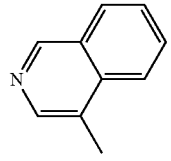 | — | 390 | >260 |
| 44. | 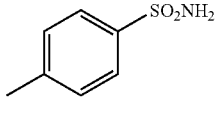 | 0 |  | — | 444 | >260 |

TABLE-continued (I)

| No. | R₁ | n | Ar | Salt | M + H | m.p. (° C.) |
|---|---|---|---|---|---|---|
| 45. | 4-methylisoquinolin-1-yl | 0 | 4-COOH-phenyl | — | 409 | >260 |
| 46. | NH₂ | 0 | pyridin-4-yl | — | 254 | >260 |
| 47. | (CH₃)₂CHCH₂C(O)NH– | 0 | pyridin-4-yl | — | 338 | >260 |
| 48. | PhCH₂CH₂C(O)NH– | 0 | pyridin-4-yl | — | 386 | 240 |
| 49. | NO₂ | 0 | pyridin-4-yl | — | 284 | >260 |
| 50. | I | 0 | pyridin-4-yl | — | 365 | >260 |
| 51. | CN | 0 | pyridazin-4-yl | — | 254 | >250 |
| 52. | CH₂NH₂ | 0 | pyridin-4-yl | CH₃SO₃H (1/1) | 268 | >250 |
| 53. | Br | 0 | pyridin-4-yl | — | 317 | >250 |

TABLE-continued (I)

| No. | R₁ | n | Ar | Salt | M + H | m.p. (°C.) |
|---|---|---|---|---|---|---|
| 54. | (3-pyridyl)-NHC(O)-(4-methylpyridin-3-yl) | 0 | 4-methylpyridyl | — | 450 | >250 |
| 55 | PhCH₂CH₂C(O)NH-(4-methylisoquinolin-8-yl) | 0 | 4-methylpyridyl | — | 513 | 205 |
| 56. | (3-pyridyl)C(O)NH-(4-methylisoquinolin-8-yl) | 0 | 4-methylpyridyl | HCl (1/1) | 486 | >250 |
| 57. | PhCH₂NH-(4-methylisoquinolin-8-yl) | 0 | 4-methylpyridyl | — | 471 | >250 |
| 58. | PhC(O)NH-(4-methylisoquinolin-8-yl) | 0 | 4-methylpyridyl | — | 485 | >250 |

TABLE-continued
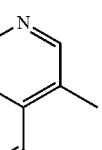
(I)
| No. | R₁ | n | Ar | Salt | M + H | m.p. (°C.) |
|---|---|---|---|---|---|---|
| 59. | 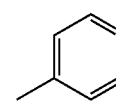 | 0 | 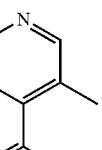 | — | 513 | 209-211 |
| 60. | 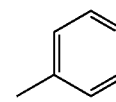 | 0 | 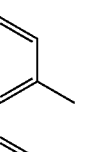 | — | 485 | 241-243 |
| 61. | 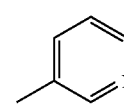 | 1 | 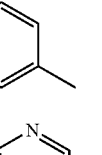 | — | 330 | >250 |
| 62. | 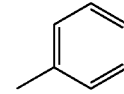 | 0 | 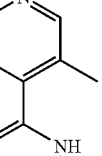 | — | 315 | >250 |
| 63. | 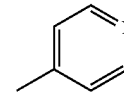 | 0 | 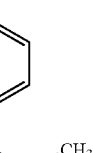 | — | 423 | >250 |
| 64. | 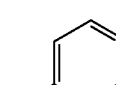 | 0 | 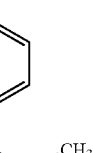 | — | 407 | >250 |

TABLE-continued (I)

| No. | R₁ | n | Ar | Salt | M + H | m.p. (° C.) |
|-----|----|----|----|------|-------|-------------|
| 65. | 2H-tetrazol-5-yl | 0 | 4-pyridyl | HCl (1/1) | 307 | >250 |
| 66. | 3-pyridyl | 0 | 4-(NHSO₂CH₃)phenyl | HCl (1/1) | 408 | >250 |
| 67. | thiazol-5-yl | 0 | 4-pyridyl | — | 322 | >250 |
| 68. | 1H-pyrrolo[2,3-c]pyridin-4-yl | 0 | 4-pyridyl | — | 355 | >250 |
| 69. | quinolin-3-yl | 0 | 4-pyridyl | — | 366 | >250 |
| 70. | 1H-pyrazol-4-yl | 0 | 4-pyridyl | — | 345 | — |
| 71. | 6-chloro-pyridin-3-yl | 0 | 4-pyridazinyl | — | 305 | >250 |
| 72. | oxazol-5-yl | 0 | 4-pyridyl | — | 350 | — |
| 73. | isoquinolin-4-yl | 0 | 3-(NHCH₂CH₃)phenyl | HCl (2/1) | 306 | — |

TABLE-continued
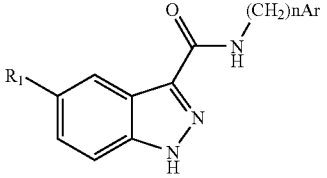
(I)
| No. | R₁ | n | Ar | Salt | M + H | m.p. (°C.) |
|---|---|---|---|---|---|---|
| 74. | 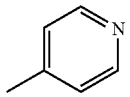 | 0 | 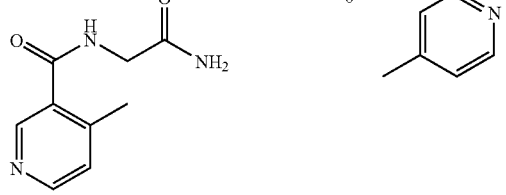 | — | 422 | — |
| 75. | 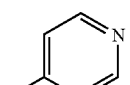 | 0 |  | — | 430 | — |
| 76. | 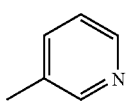 | 1 |  | — | 336 | 248 |
| 77. | 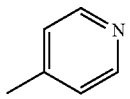 | 0 |  | — | 317 | — |
| 78. | 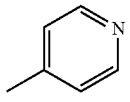 | 0 |  | — | 388 | — |
| 79. | 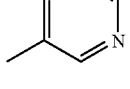 | 1 |  | — | 330 | — |
| 80. | 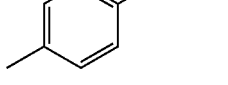 | 0 |  | — | 394 | — |
| 81. | 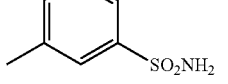 | 0 |  | — | 394 | — |
| 82. | 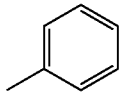 | 0 |  | — | 315 | — |

TABLE-continued
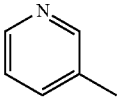
(I)
| No. | R₁ | n | Ar | Salt | M + H | m.p. (° C.) |
|---|---|---|---|---|---|---|
| 83. | 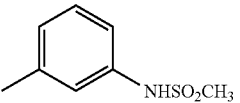 | 0 | 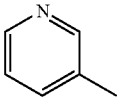 | — | 408 | — |
| 84. | 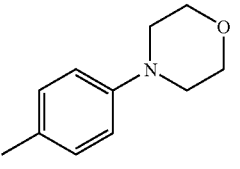 | 0 | 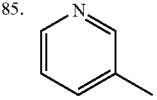 | — | 400 | >260 |
| 85. | 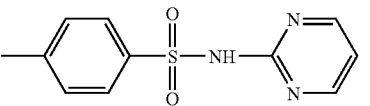 | 0 | 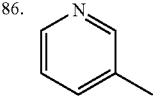 | — | 472 | >260 |
| 86. | 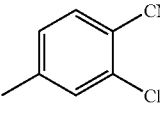 | 0 | 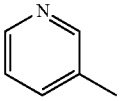 | — | 374 | >260 |
| 87. | 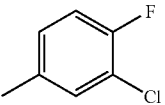 | 0 | 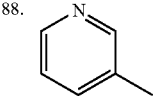 | — | 367 | >260 |
| 88. | 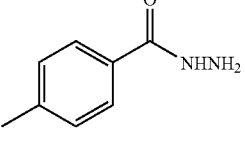 | 0 | 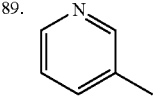 | — | 373 | >260 |
| 89. | 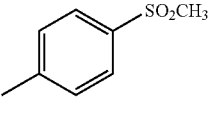 | 1 | 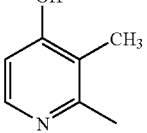 | — | 407 | >260 |
| 90. | 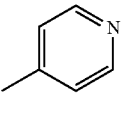 | 0 | 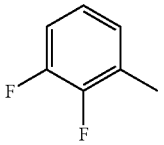 | — | 346 | — |
| 91. | 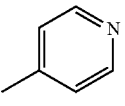 | 0 | 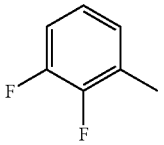 | — | 351 | — |

TABLE-continued
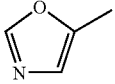
(I)
| No. | R₁ | n | Ar | Salt | M + H | m.p. (°C.) |
|---|---|---|---|---|---|---|
| 92. | 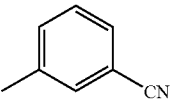 | 0 | 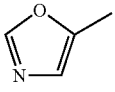 | — | 330 | >250 |
| 93. | 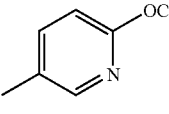 | 0 | 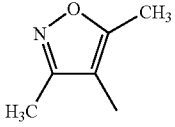 | — | 336 | 235 (dec.) |
| 94. | 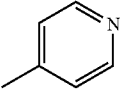 | 0 | 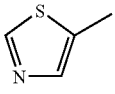 | — | 334 | >250 |
| 95. | 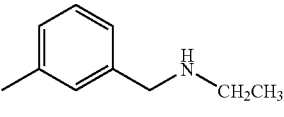 | 0 | 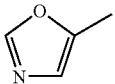 | — | 378 | 182 |
| 96. | 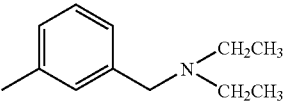 | 0 | 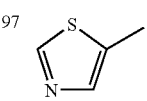 | — | 390 | 224 |
| 97 | 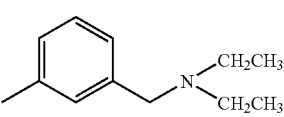 | 0 | 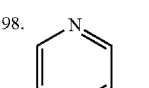 | — | 406 | — |
| 98. | 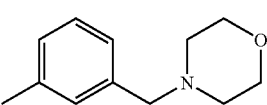 | 0 | 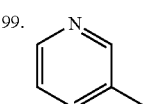 | — | 414 | 160 (dec.) |
| 99. | 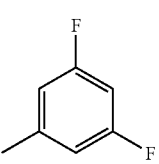 | 1 | 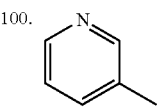 | — | 365 | >260 |
| 100. | 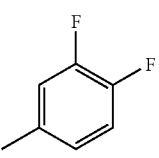 | 1 | | — | 365 | >260 |

The compound of the invention have been the subject of pharmacology trials which have shown their value as active substances in therapy.

They were in particular tested for their effects of inhibiting certain cyclin dependent kinases (cdks) such as cdk1 (also called cdc2), cdk2 and cdk4.

The cdks are protein (serine/threonine) kinases which play a decisive role in the progression of the cell cycle, functioning solely on being associated with cyclins. Within these associations, the cyclins have a control function, whereas the function of the cdks is catalytic.

To date, nine cdks (cdk1 to cdk9) and eleven cyclins have been identified in humans. The individual cdks play distinct roles in the progression of the cell cycle and can be classified according to the stage of the cell cycle in which they are involved: G1/S transition (cdk2/cyclin E, cdk4/cyclin D1-D3, cdk6/cyclin D1, cdk8/cyclin C), S phase (cdk2/cyclin A), G2 phase (cdc2/cyclin A), G2/M transition (cdc2/cyclin B, cdk7/cyclin H).

For example, the active cdk4/cyclin D and cdk6/cyclin D phosphorylate the retinoblastoma protein pRb leading to its dissociation of the transcription factor complex E2F/PD1 and thus deactivating its transcription suppressor activity. The result of the release of E2F/DP1 is the activation of the transcription of a group of genes necessary for entering into the S phase, including thymidylate synthetase, dihydrofolate reductase and cyclin E. At the end of the G1 stage, cyclin E stimulates cdk2 which acts by continuing the process of phosphorylation of pRb, having the result of an irreversible engagement in a cell division and transition to S phase process. During the S phase, cyclin A replaces cyclin E by activating cdk2, this having the result of a change in the specificity of the cdk2 substrate. E2F/DP1 is phosphorylated, which inactivates its transcription promoter activity. This results in a decrease in the synthesis of cyclin E and a transition to G2.

The activity of the cdks is inhibited by the endogenous cdk inhibitors (cdkI: p15, p16, p18, p19, p21, p27 and p57).

The development of tumours in humans is often associated with a deregulation of the cdk activity. p16, a cdk4 and cdk6 inhibitor, is destroyed or mutated in 55% of glyomas and mesotheliomas and in 38% of cancers of the pancreas. It has been shown that p27, another inhibitor, and the cyclin E and cyclin D coactivators are respectively "overexpressed" or "underexpressed", in especially breast, colon, non-small cell lung, stomach, prostate, bladder, nonhodgkin lymphoma and ovarian cancers. It has been shown that their altered expression can be correlated with an increase in the cdk2 and cdk4 activities.

The induction of p21 by the activated tumour suppressor p53, in response to the signals for alteration of DNA, inhibits the activity of cdk2 (the key component in the control of the G1 phase); thus, the mutation of p53 in about 50% of all human cancers can indirectly result in the deregulation of the cdk activity and the loss of the control of the G1 phase, contributing to the generation of tumours (Paulovich A et al., Cell. 88, 315-321 (1997)).

The compounds of the invention represent a novel class of cdk inhibitors, whose properties include the suspension of the cell cycle, the blocking of the proliferation of cells and apoptosis.

The inhibitory activity on cdk2 has been demonstrated in a test where the enzymatic cdk2/cyclin A activity is measured by quantification of $^{33}$P obtained from $^{33}$P-ATP which was incorporated into the type III-S histone of calf thymus (Sigma Ref: H-5505). The trial is carried out in 50 mM HEPES medium, pH 7.2, in the presence of 1 mM DTT (added at the time of use), 1 mM MgCl$_2$, 1 mM EGTA and 0.02% Tween 20. The histone concentration is 0.4 mg/ml and the cold ATP concentration is 10 µM. The concentration of $^{33}$P-ATP is adjusted to an activity of about 300 000 cpm. The inhibitor 5 µl is added in solution in 10% aqueous DMSO in order to have a final concentration of 1% DMSO. The reaction mixture is incubated for 1 hour at room temperature. The reaction is stopped by depositing on a filter (Whatman P81, ion-exchange chromatography paper). The filters are washed twice by dipping for 20 min in a 37.5 mM phosphoric acid solution. The filters are placed in scintillation vials and the scintillant (aquasafe, Zinsser Analytic, 5 ml) is added. These vials are then counted for 1 min on a Wallac counter.

Under these conditions, the most active compounds of the invention have IC$_{50}$ values (concentration inhibiting 50% of the enzymatic activity) of less than 20 µM.

The inhibitory activity on cdk1 was demonstrated in a cdk1/cyclin B test. The measurement of the inhibitory activity of the compounds of the invention on cdk1 is carried out according to the same procedure as for the cdk2/cyclin A test with the following modifications: MgCl$_2$ concentration is 10 mmol and the ATP concentration is 0.1 µM.

Under these conditions, the most active compounds of the invention exhibit IC$_{50}$ (concentration inhibiting 50% of the enzymatic activity) values of less than 20 µM.

The inhibitory activity on cdk4 was demonstrated in a cdk4/cyclin D1 test. The measurement of the inhibitory activity of the compounds of the invention on cdk4 is carried out according to the same procedure as for the cdk1/cyclin B test.

The only difference is the substrate which may be the retinoblastoma protein at a concentration of 0.02 mg/ml or the peptide K10K (K-A-P-L-S-P-K-K-A-K-NH$_2$) at a concentration of 1 mM.

Under these conditions, the most active compounds of the invention exhibit IC$_{50}$ (concentration inhibiting 50% of the enzymatic activity) values of less than 20 µM.

The results of the biological tests show that the compounds of the invention are inhibitors of cdk1, cdk2 and cdk4.

Thus, the compounds of the invention may be used in the treatment of pathologies in which an inhibitor of cdk1, cdk2 and cdk4 provides a therapeutic benefit. In particular, such pathologies are cancers, autoimmune and/or inflammatory diseases, cardiovascular diseases, neurodegenerative diseases, viral and fungal infections, degenerative diseases of the musculoskeletal system, haematological diseases, kidney diseases and liver diseases caused by toxins or alcohol.

The compounds of the invention have demonstrated in particular a powerful antiproliferative activity on certain tumour cell lines.

Furthermore, given the key role of cdks in the regulation of the proliferation of cells in general, the inhibitors of the invention can behave as reversible cytostatic agents which can be used in the treatment of disease processes exhibiting abnormal cell proliferation characteristics.

The compounds of general formula (I) are also capable of modulating apoptosis, a process of physiological cell death, which is crucial for normal development and haemostasis. Alterations in apoptosis contribute to the pathogenesis of a multiplicity of human diseases. The compounds of general formula (I), as apoptosis modulator, may be useful for the treatment of human diseases exhibiting aberrations in apoptosis. Finally, the cdk inhibitors of the invention may be used in the treatment of viral and fungal diseases since cdks are activated by viral cyclin (v-cyclin) and are therefore involved in viral replication and the proliferation of viruses such as the herpesvirus and HIV-1.

More specifically, the compounds of general formula (I) may be useful in the treatment:

- of cancers, including but not limited to carcinoma, including bladder, breast, colon, kidney, liver, lung, ovarian, pancreatic, stomach, uterine, thyroid, prostate and skin cancer; haematopoietic tumours of the lymphoid family, including acute lymphocytic leukaemia, follicular lymphomas, B cell lymphoma and Burkett's lymphoma; haematopoietic tumours of the myeloid family, including acute and chronic myeloid leukaemias and promyelocytic leukaemia; tumours of mesenchymal origin including fibrosarcoma and rhabdomyosarcoma; and other tumours, including melanoma, seminoma, teratocarcinoma, osteosarcoma, neuroblastoma and glyoma, and precancerous lesions such as hereditary adenomatous polyposis;
- autoimmune or inflammatory diseases: including but not limited to arthritis, such as rheumatoid arthritis, psoriasis, immune glomerulonephritis, intestinal inflammation, transplant rejection and endotoxic shock, systemic lupus, erythematosis, autoimmune diabetes mellitus, pigmentary retinitis;
- cardiovascular diseases: including but not limited to neurofibromatosis, atherosclerosis, pulmonary fibrosis, restenosis following angioplasty or vascular surgery, the formation of a hypertrophic scar, angiogenesis, vein graft disease, transplantation vasculopathy, ischaemic lesions following myocardial infarction, lesions caused by a stroke or a reperfusion, cardiac arrhythmia;
- neurodenerative diseases, including but not limited to Alzheimer's diseases, AIDS-related dementia, Parkinson's disease, amyotrophic lateral sclerosis, retinitis pigmentosa, muscular spinal atrophy, cerebellum degeneration;
- viral and fungal infections, including but not limited to the herpesvirus, the smallpox virus, the Epstein-Barr virus, the Sindbis virus, the adenovirus and the AIDS virus;
- degenerative diseases of the musculoskeletal system, including but not limited to osteoporosis and arthritis, rhinosinusitis reactive to aspirin, cystic fibrosis;
- haematological diseases, including but not limited to chronic anaemia, aplastic anaemia and myeloplastic syndromes.

Furthermore, the compounds of general formula (I) may be used for treating alopecia caused by chemotherapy, thrombocytopenia caused by chemotherapy, leukopenia or mucositis caused by chemotherapy.

The use of the compounds of general formula (I), and of the following compounds, for the preparation of a medicament intended for treating the pathologies mentioned above forms an integral part of the invention:

—N-phenyl-1H-indazole-3-carboxamide
—N-(2-chlorophenyl)-1H-indazole-3-carboxamide
—N-(3-chlorophenyl)-1H-indazole-3-carboxamide
—N-(4-chlorophenyl)-1H-indazole-3-carboxamide
—N-(2,4-dichlorophenyl)-1H-indazole-3-carboxamide
—N-(3,4-dichlorophenyl)-1H-indazole-3-carboxamide
—N-(2-methylphenyl)-1H-indazole-3-carboxamide
—N-(2,4-dimethylphenyl)-1H-indazole-3-carboxamide
—N-(2-methoxyphenyl)-1H-indazole-3-carboxamide
—N-(4-methoxyphenyl)-1H-indazole-3-carboxamide
—N-(4-thiomethylphenyl)-1H-indazole-3-carboxamide
—N-(3-chloro-4-thiomethylphenyl)-5-amino-1H-indazole-3-carboxamide
—N-benzyl-1H-indazole-3-carboxamide
—N-(2-chlorobenzyl)-1H-indazole-3-carboxamide
—N-(4-methylbenzyl)-1H-indazole-3-carboxamide
—N-(pyridin-2-ylmethyl)-1H-indazole-3-carboxamide
—N-(pyridin-3-ylmethyl)-1H-indazole-3-carboxamide
—N-(pyridin-4-ylmethyl)-1H-indazole-3-carboxamide
—N-(2-phenylethyl)-1H-indazole-3-carboxamide
—N-(3,4-dimethoxyphenylethyl)-1H-indazole-3-carboxamide
—N-[3-(pyridin-2-yl)propyl]-1H-indazole-3-carboxamide
—N-[3-(2,6-dimethylphenyl)propyl]-5-nitro-1H-indazole-3-carboxamide The subject of the invention is also medicaments which comprise a compound of general formula (I) or an addition salt thereof with a pharmaceutically acceptable acid or alternatively a hydrate or solvate of the compound of general formula (I). These medicaments find their use in therapy, in particular in the treatment of the pathologies mentioned above.

According to another of its aspects, the present invention relates to pharmaceutical compositions comprising, as active ingredient, at least one compound according to the invention. These pharmaceutical compositions comprise an effective dose of a compound according to the invention, or a pharmaceutically acceptable salt, a hydrate or a solvate of the said compound, and optionally one or more pharmaceutically acceptable excipients.

The said excipients are chosen according to the pharmaceutical dosage form and the desired mode of administration from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active ingredient of general formula (I) above, or its possible salt, solvate or hydrate, may be administered in a unit form for administration, as a mixture with conventional pharmaceutical excipients, to animals or to human beings for the prophylaxy or the treatment of the above disorders or diseases.

The appropriate unit forms for administration comprise the forms for oral administration such as tablets, soft or hard gelatin capsules, powders, granules, chewing gums or oral solutions or suspensions, the forms for sublingual, buccal, intratracheal, intraocular or intranasal administration, or for administration by inhalation, the forms for subcutaneous, intramuscular or intravenous administration and the forms for rectal or vaginal administration. For topical application, it is possible to use the compounds according to the invention in creams, ointments or lotions.

By way of example, a unit form for administration of a compound according to the invention in tablet form may comprise the following components:

| | |
|---|---|
| Compound according to the invention | 50.0 mg |
| Mannitol | 223.75 mg |
| Croscaramellose sodium | 6.0 mg |
| Maize starch | 15.0 mg |
| Hydroxypropylmethylcellulose | 2.25 mg |
| Magnesium stearate | 3.0 mg |

In order to obtain the desired prophylactic or therapeutic effect, the dose of active ingredient may vary between 0.1 mg and 200 mg per kg of body weight and per day. Although these dosages are examples of an average situation, there may be particular cases where higher or lower dosages are appropriate, such dosages also belong to the invention. According to the usual practice, the dosage appropriate for each patient is determined by the doctor according to the mode of administration, the weight and the response of the said patient.

Each unit dose may contain from 0.1 to 1 000 mg, preferably from 0.1 to 500 mg, of active ingredient in combination with one or more pharmaceutical excipients. This unit dose may be administered 1 to 5 times per day so as to administer a daily dosage of 0.5 to 5 000 mg, preferably from 0.5 to 2 500 mg.

The present invention, according to another of its aspects, also relates to a method for treating the pathologies indicated above which comprise the administration of a compound according to the invention, of a pharmaceutically acceptable salt, of a solvate or of a hydrate of the said compound.

The invention claimed is:

1. A compound corresponding to general formula (I):

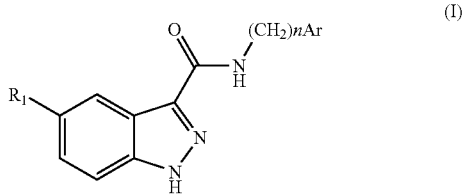

in which, $R_1$ represents a heteroaromatic group optionally substituted with one or two substituents selected from a halogen atom, a hydroxyl, a heteroaromatic group, $C_{1-6}$ alkyl, $NH_2$, $NHR_2$, $NHCOR_2$, $COOR_2$, $CONH_2$, $CONHR_2$ and $CH_2XR_2$ where X represents an atom selected from O, NH and S; and Ar represents a heteroaromatic group, optionally substituted with one or two substituents selected from a halogen atom, $C_{1-6}$ alkyl, $C_{1-6}$ thioalkyl, $C_{1-6}$ alkoxy, $CH_2OH$, phenoxy, morpholinyl, —$CH_2$-morpholinyl, $NH_2$, $NHR_2$, $NR_2R_3$, $NHSO_2R_2$, CN, $SO_2R_2$, $SO_2NH_2$, $SO_2NHR_2$, COOH, $COOR_2$, $CONH_2$, $CONHNH_2$, $CONHR_2$, $CH_2NHR_2$ and $CH_2NR_2R_3$; and wherein $R_2$ and $R_3$ represent, independently of each other, a $C_{1-6}$ alkyl optionally substituted with a $CONH_2$ group, with a phenyl or with a heteroaromatic group; or $R_2$ and $R_3$ represent, independently of each other, a phenyl or a heteroaromatic group; and n represents 0, 1, 2 or 3; or a salt thereof, or a hydrate or a solvate thereof.

2. The compound according to claim 1, wherein:

$R_1$ represents a heteroaromatic group optionally substituted with one or two substituents selected from a halogen atom, a hydroxyl, a heteroaromatic group, $C_{1-6}$ alkyl, $NH_2$, $NHR_2$, $NHCOR_2$, $COOR_2$, $CONH_2$, $CONHR_2$ and $CH_2XR_2$ where X represents an atom selected from O, NH and S;

Ar represents a heteroaromatic group, optionally substituted with one or two substituents selected from a halogen atom, $C_{1-6}$ thioalkyl, $C_{1-6}$ alkoxy, $CH_2OH$, phenoxy, morpholinyl, —$CH_2$-morpholinyl, $NH_2$, $NHR_2$, $NR_2R_3$, $NHSO_2R_2$, CN, $SO_2R_2$, $SO_2NH_2$, $SO_2NHR_2$, COOH, $COOR_2$, $CONH_2$, $CONHNH_2$, $CONHR_2$, $CH_2NHR_2$ and $CH_2NR_2R_3$; and wherein $R_2$ and $R_3$ represent, independently of each other, a $C_{1-6}$ alkyl optionally substituted with a $CONH_2$ group, with a phenyl or with a heteroaromatic group; or $R_2$ and $R_3$ represent, independently of each other, a phenyl or a heteroaromatic group; and n represents 0, 1, or 2; or a salt thereof, or a hydrate or a solvate thereof.

3. The compound of general formula (I) according to claim 1, wherein:

when $R_1$ represents a heteroaromatic group optionally substituted with one or two substituents selected from a halogen atom, a hydroxyl, a heteroaromatic group, $C_{1-6}$ alkyl, $NH_2$, $NHR_2$, $NHCOR_2$, $COOR_2$, $CONH_2$, $CONHR_2$ and $CH_2XR_2$ where X represents an atom selected from O, NH and S;

then Ar represents a heteroaromatic group, optionally substituted with one or two substituents selected from a halogen atom, $C_{1-6}$ alkyl, $C_{1-6}$ thioalkyl, $C_{1-6}$ alkoxy, $CH_2OH$, phenoxy, morpholinyl, —$CH_2$-morpholinyl, $NH_2$, $NHR_2$, $NR_2R_3$, $NHSO_2R_2$, CN, $SO_2R_2$, $SO_2NH_2$, $SO_2NHR_2$, COOH, $COOR_2$, $CONH_2$, $CONHNH_2$, $CONHR_2$, $CH_2NHR_2$ and $CH_2NR_2R_3$; and wherein $R_2$ and $R_3$ represent, independently of each other, a $C_{1-6}$ alkyl optionally substituted with a $CONH_2$ group, with a phenyl or with a heteroaromatic group; or $R_2$ and $R_3$ represent, independently of each other, a phenyl or a heteroaromatic group; and n represents 0 or 1; or a salt thereof, or a hydrate or a solvate thereof.

4. The compound of general formula (I) according to claim 1, wherein:

when $R_1$ represents a heteroaromatic group chosen from pyrazolyl, tetrazolyl, thiazolyl, oxazolyl, pyridinyl, pyrimidinyl, quinolinyl, isoquinolinyl or pyrrolo [2,3-c]pyridinyl, optionally substituted with one or two substituents chosen from a chlorine or a fluorine, a hydroxyl, a pyridinyl, a methyl, $NH_2$, $NHR_2$, $NHCOR_2$, $COOR_2$, $CONH_2$, $CONHR_2$ and $CH_2OR_2$;

then Ar represents pyridinyl, optionally substituted with a $C_{1-6}$ alkoxy; and wherein $R_2$ represents a methyl, an ethyl or a 2-methylpropyl, optionally substituted with a group $CONH_2$ or with a phenyl; or $R_2$ represents a phenyl or a heteroaromatic group chosen from a pyridinyl or a pyrimidinyl; and n represents 0 or 1;

or a salt thereof, or a hydrate or a solvate thereof.

5. The compound of general formula (I) according to claim 1, wherein:

$R_1$ represents a heteroaromatic group optionally substituted with one or two substituents chosen from a halogen atom, a hydroxyl, a heteroaromatic group, $C_{1-6}$ alkyl, $NH_2$, $NHR_2$, $NHCOR_2$, $COOR_2$, $CONH_2$, $CONHR_2$ and $CH_2XR_2$ where X represents an atom chosen from O, NH and S;

Ar represents a heteroaromatic group, optionally substituted with one or two substituents chosen from fluorine, chlorine, methoxy, $CH_2OH$, phenoxy, morpholinyl, —$CH_2$-morpholinyl, $NH_2$, $NHSO_2CH_3$, CN, $SO_2CH_3$, $SO_2NH_2$, $SO_2NH$-pyrimidinyl, COOH, $CONH_2$, $CONHNH_2$, $CH_2NHC_2H_5$ and $CH_2N(C_2H_5)_2$; and n represents 0, 1, 2 or 3;

or a salt thereof, or a hydrate or a solvate thereof.

6. The compound of general formula (I) according to claim 1, wherein:

R₁ represents a heteroaromatic group chosen from pyrazolyl, thiazolyl, oxazolyl, pyridinyl, isoquinolinyl or pyrrolo[2,3-c]pyridinyl, optionally substituted with one or two substituents chosen from a chlorine, a pyridinyl, methyl, NH₂ and CONHR₂;

Ar represents
a pyridinyl, optionally substituted with a methoxy;
R₂ represents a methyl or an ethyl, optionally substituted with a group CONH₂, or with a phenyl; or R₂ represents a pyridinyl or a pyrimidinyl; and
n represents 0 or 1;
or a salt thereof, or a hydrate or a solvate thereof.

7. The compound of formula (I) according to claim 1, which is selected from the group consisting of:
—N-(pyridin-4-yl)-5-pyridin-3-yl-1H-indazole-3-carboxamide hydrochloride;
—N-(pyridin-4-yl)-5-(4-methyl-[3,4']bipyridinyl-5-yl)-1H-indazole-3-carboxamide hydrochloride;
—N-(pyridin-4-yl)-5-isoquinolin-4-yl-1H-indazole-3-carboxamide;
—N-(pyridin-3-ylmethyl)-5-isoquinolin-4-yl-1H-indazole-3-carboxamide;
—N-(pyridin-4-yl)-5-[4-methyl-5-(pyridin-3-ylcarbamoyl)pyridin-3-yl]-1H-indazole-3-carboxamide;
—N-(pyridin-4-yl)-5-(4-methyl-[3,3']bipyridinyl-5-yl)-1H-indazole-3-carboxamide;
—N-(pyridin-4-yl)-5-(1,3-thiazol-5-yl)-1H-indazole-3-carboxamide;
—N-(pyridin-4-yl)-5-(1H-pyrrolo[2,3-c]pyridin-4-yl)-1H-indazole-3-carboxamide;
-5-(1H-pyrazol-4-yl)-N-(pyridin-4-yl)-1H-indazole-3-carboxamide;
—N-(pyridin-4-yl)-5-[(2-chloro)pyridin-5-yl]-1H-indazole-3-carboxamide;
-5-(1,3-oxazol-5-yl)-N-(pyridin-4-yl)-1H-indazole-3-carboxamide;
-5-(5-amino-4-methylpyridin-3-yl)-N-(pyridin-4-yl)-1H-indazole-3-carboxamide;
—N-(pyridin-4-yl)-5-(3-(N-aminoketomethyl)carboxamide)pyridin-4-yl-1H-indazole-3-carboxamide;
—N-(pyridin-3-ylmethyl)-5-(1,3-thiazol-5-yl)-1H-indazole-3-carboxamide;
—N-(pyridin-3-ylmethyl)-5-pyridin-3-yl-1H-indazole-3-carboxamide;
-5-(4-hydroxy-3-methylpyridin-2-yl)-N-pyridin-4-yl-1H-indazole-3-carboxamide;
—N-(2-methoxypyridin-5-yl)-5-(1,3-oxazol-5-yl)-1H-indazole-3-carboxamide;
or a salt thereof, or a hydrate or a solvate thereof.

8. A method for preparing a compound of general formula (I) of claim 1, comprising the step consisting in deprotecting a compound of general formula (VII)

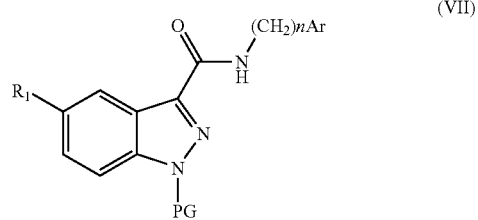

in which R₁, Ar and n are as defined in general formula (I) according to claim 1 and PG represents a protecting group of the trimethylsilylethoxymethyl (SEM) or mesitylenesulphonyl (Mts) type, either by the action of a base such as sodium hydroxide, or in the presence of tetrabutylammonium fluoride (TBAF) and ethylenediamine, or alternatively in the presence of trifluoroacetic acid followed by heating with ethylenediamine.

9. The method of preparation according to claim 8, wherein the compound of general formula (VII),

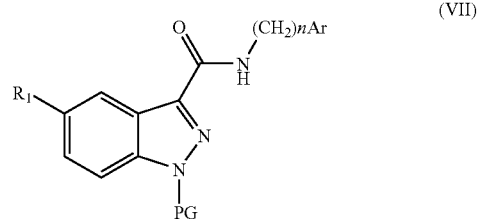

in which R₁, Ar and n are as defined in general formula (I) according to claim 1 and PG represents a protecting group of the trimethylsilylethoxymethyl (SEM) or mesitylenesulphonyl (Mts) type,
is prepared by coupling a compound of general formula (V)

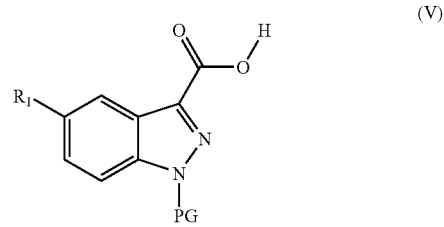

in which R₁ is as defined in general formula (I) according to claim 1 and PG represents a protecting group of the trimethylsilylethoxymethyl (SEM) or mesitylenesulphonyl (Mts) type,
with an amine of general formula Ar(CH₂)nNH₂ (VI) in which Ar and n are as defined in general formula (I) according to claim 1, it being possible for the coupling reaction to be carried out by activating the compound of general formula (V) with coupling reagents, such as carbonyldiimidazole or isopropyl or isobutyl chloroformate.

10. A compound of general formula (V)

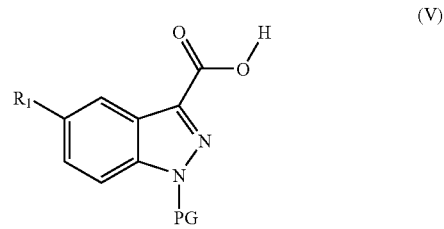

in which
R₁ represents
a heteroaromatic group optionally substituted with one or two substituents selected from a halogen atom, a hydroxyl, a heteroaromatic group, $C_{1-6}$ alkyl, $NH_2$, $NHR_2$, $NHCOR_2$, $COOR_2$, $CONH_2$, $CONHR_2$ and $CH_2XR_2$ where X represents an atom selected from O, NH and S; and PG represents a protecting group of the trimethylsilylethoxymethyl (SEM) or mesitylenesulphonyl (Mts) type.

11. A compound of general formula (VII)

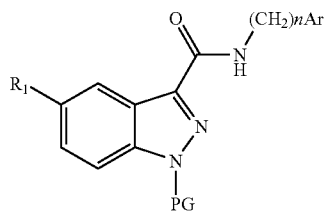

(VII)

in which $R_1$ represents a heteroaromatic group optionally substituted with one or two substituents selected from a halogen atom, a hydroxyl, a heteroaromatic group, $C_{1-6}$ alkyl, $NH_2$, $NHR_2$, $NHCOR_2$, $COOR_2$, $CONH_2$, $CONHR_2$ and $CH_2XR_2$ where X represents an atom selected from O, NH and S;

Ar represents a heteroaromatic group, optionally substituted with one or two substituents selected from a halogen atom, $C_{1-6}$ alkyl, $C_{1-6}$ thioalkyl, $C_{1-6}$ alkoxy, $CH_2OH$, phenoxy, morpholinyl, $NH_2$, $NHR_2$, $NR_2R_3$, $NHSO_2R_2$, CN, $SO_2R_2$, $SO_2NH_2$, $SO_2NHR_2$, COOH, $COOR_2$, $CONH_2$, $CONHNH_2$, $CONHR_2$ and $CH_2NHR_2$; and wherein $R_2$ and $R_3$ represent, independently of each other, a $C_{1-6}$ alkyl optionally substituted with a $CONH_2$, a phenyl or a heteroaromatic group; or $R_2$ and $R_3$ represent, independently of each other, a phenyl or a heteroaromatic group;

n represents 0, 1, 2 or 3; and

PG represents a protecting group of the trimethylsilylethoxymethyl (SEM) or mesitylenesuiphonyl (Mts) type.

12. A compound of general formula (X)

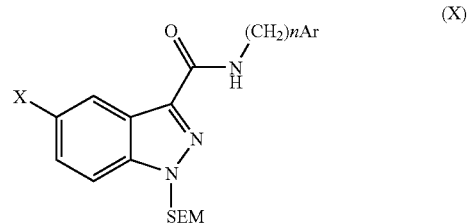

(X)

in which

Ar represents a heteroaromatic group, optionally substituted with one or two substituents selected from a halogen atom, $C_{1-6}$ alkyl, $C_{1-6}$ thioalkyl, $C_{1-6}$ alkoxy, $CH_2OH$, phenoxy, morpholinyl, $NH_2$, $NHR_2$, $NR_2R_3$, $NHSO_2R_2$, CN, $SO_2R_2$, $SO_2NH_2$, $SO_2NHR_2$, COOH, $COOR_2$, $CONH_2$, $CONHNH_2$, $CONHR_2$ and $CH_2NHR_2$; and wherein $R_2$ and $R_3$ represent, independently of each other, a $C_{1-6}$ alkyl optionally substituted with a $CONH_2$, a phenyl or a heteroaromatic group; or $R_2$ and $R_3$ represent, independently of each other, a phenyl or a heteroaromatic group;

n represents 0, 1, 2 or 3;

SEM represents a protecting group of trimethylsilylethoxymethyl type; and

X represents a bromine or iodine atom.

13. A pharmaceutical composition comprising at least one compound of general formula (I) according to claim 1, or a pharmaceutically acceptable salt, hydrate or solvate thereof, in combination with one or more pharmaceutically acceptable excipients.

\* \* \* \* \*